US007408554B2

(12) United States Patent
Lawson, Jr. et al.

(10) Patent No.: US 7,408,554 B2
(45) Date of Patent: Aug. 5, 2008

(54) SPHERICAL MODELING TOOL

(76) Inventors: Phillip W. Lawson, Jr., 24181 Supai Rd., Indian Hills, CO (US) 80454; Robert L. Lindstrom, 3721 Chevy Chase Dr., La Canada Flintridge, CA (US) 91011

( * ) Notice: Subject to any disclaimer, the term of this patent is extended or adjusted under 35 U.S.C. 154(b) by 379 days.

(21) Appl. No.: 10/939,305

(22) Filed: Sep. 10, 2004

(65) Prior Publication Data

US 2005/0102316 A1    May 12, 2005

Related U.S. Application Data

(60) Provisional application No. 60/501,798, filed on Sep. 10, 2003.

(51) Int. Cl.
  *G06T 11/20* (2006.01)
(52) U.S. Cl. .................. 345/442; 345/440; 345/441
(58) Field of Classification Search .................. 345/440, 345/441, 442
  See application file for complete search history.

(56) References Cited

U.S. PATENT DOCUMENTS

| 5,039,937 | A | * | 8/1991 | Mandt et al. | ............. | 324/121 R |
| 5,491,781 | A | * | 2/1996 | Gasperina | .................... | 715/786 |
| 5,553,225 | A | * | 9/1996 | Perry | ........................ | 715/786 |
| 5,910,268 | A | * | 6/1999 | Keefer | ........................ | 219/728 |
| 2002/0055919 | A1 | * | 5/2002 | Mikheev | ........................ | 707/3 |
| 2002/0080150 | A1 | * | 6/2002 | Nakatani | .................... | 345/660 |
| 2003/0065260 | A1 | * | 4/2003 | Cheng et al. | ................. | 600/427 |
| 2004/0030741 | A1 | * | 2/2004 | Wolton et al. | ................ | 709/202 |
| 2005/0102316 | A1 | * | 5/2005 | Lawson et al. | ............... | 707/102 |

FOREIGN PATENT DOCUMENTS

EP          1217507 A2 *  6/2002

OTHER PUBLICATIONS

Wavelets over curvilinear grids Gregory M. Nielson, Il-Hong Jung, Junwon Sung Oct. 1998, Proceedings of the conference on Visualization '98 VIS '98 Publisher: IEEE Computer Society Press.*
Automated conversion of curvilinear wire-frame models to surface boundary models; a topological approach John A. Brewer, S. Mark Courter Aug. 1986, ACM SIGGRAPH Computer Graphics, Proceedings of the 13th annual conference on Computer graphics and interactive techniques SIGGRAPH '86, vol. 20 Issue 4 Publisher: ACM Press.*

(Continued)

*Primary Examiner*—Javid A Amini
(74) *Attorney, Agent, or Firm*—Kirkpatrick & Lockhart Preston Gates Ellis LLP

(57) ABSTRACT

In one aspect, the invention relates to a method for analyzing qualitative data. The method includes the step of providing a plurality of evaluation categories and a respective ranking system. Providing a closed curvilinear graph in which each unit of radius corresponds to a rank in the ranking system is another step of the method. Another step in the method includes placing each evaluation category at a location on the circumference of the closed curvilinear graph. The steps of the method also include providing the evaluation categories and ranking system to an entity being evaluated. The entity selects a rank in response in each respective category according to the method. Plotting the ranking of each respective category as a node in the closed curvilinear graph in response to the ranking by the entity is another step in the method.

29 Claims, 22 Drawing Sheets

OTHER PUBLICATIONS

Simplified representation of vector fields Alexandru Telea, Jarke J. van Wijk Oct. 1999, Proceedings of the conference on Visualization '99: celebrating ten years VIS '99 Publisher: IEEE Computer Society Press.*

Saddle Connectors—An Approach to Visualizing the Topological Skeleton of Complex 3D Vector Fields Holger Theisel, Tino Weinkauf, Hans-Christian Hege, Hans-Peter Seidel Oct. 2003, Proceedings of the 14th IEEE Visualization 2003 (VIS'03) VIS'03, Publisher: IEEE Computer Society.*

Accelerating Large Data Analysis By Exploiting Regularities David Ellsworth, Patrick J. Moran Oct. 2003, Proceedings of the 14th IEEE Visualization 2003 (VIS'03) VIS '03 Publisher: IEEE Computer Society.*

Accelerated ray-casting for curvilinear volumes Lichan Hong, Arie Kaufman, Oct. 1998, Proceedings of the conference on Visualization '98 VIS '98, Publisher: IEEE Computer Society Press.*

* cited by examiner

SPHERICAL MODELING TOOL

CROSS-REFERENCE TO RELATED APPLICATIONS

This application claims the benefits of and priority to U.S. Provisional Patent Application Ser. No. 60/501,798 filed on Sep. 10, 2003 the disclosures of which are hereby incorporated herein by reference in their entirety.

FIELD OF THE INVENTION

The invention relates generally to the field of data representation and analysis. Specifically, the invention relates to information representation techniques and devices.

BACKGROUND OF THE INVENTION

Various representational formats have developed over time to organize and to represent information. Specifically, organizational charts, tables, decision trees, and histograms are some of the traditional formats for organizing and reporting data. Once the underlying data is organized into a particular format, it can be used for a desired purpose. However, the utility of these traditional formats are often subject to certain limitations.

Some format specific limitations arise because the representational capacity of a given format is exceeded by the amount of data required to accurately model a system. For example, a table of data cannot represent a large and complex system without becoming voluminous and unwieldy for a human analyst to parse. As a result, tables and other formats sometimes enforce an unrealistic view of the world where only one facet of a larger system is considered in isolation. Accordingly, data representation techniques that encourage analytic approaches that expand perspectives and change outmoded norms are needed. However, other limitations result when dealing with complex systems.

Mismatches between the nature of the data format and the nature of the underlying data can lead to another data format limitation. For example, a table of increasing values may indicate a pattern at first viewing. However, without supplemental calculations, the details of the pattern remain obscured. Thus, some of the traditional representation formats introduced above are inherently limited. As such, they are best suited for simple data and systems.

In contrast, complex systems or relationships with periodic or persistent non-linear components cannot always be easily handled by traditional data representations. Flexible and intuitive approaches to data representation are needed to address these deficiencies.

Currently, data representation and analytic tools based upon conventional teachings are difficult to use. They often include non-intuitive interfaces that make it difficult to extract meaningful information about the larger system. As discussed above, various limitations exist with regard to traditional data representation formats. Consequently, a need therefore exists for techniques and apparatus that are intuitive, adaptable, and suitable for modeling complex systems or individual system components.

SUMMARY OF THE INVENTION

In one aspect, the methods and techniques discussed below are based on and designed to work in conjunction with the principles of Sphericity, a conceptual and practical philosophy developed by Phil Lawson and Robert Lindstrom and introduced in their book Being Spherical the disclosures of which are herein incorporated by reference in their entirety. The Spherical Modeling Tool (SMT) is another aspect of the claimed invention. However, the scope of the invention is not limited to one philosophical or conceptual framework, but only the scope of the claims and equivalents thereof.

In one aspect, the invention relates to a method for analyzing qualitative data. The method includes the step of providing a plurality of evaluation categories and a respective ranking system. Providing a closed curvilinear graph in which each unit of radius corresponds to a rank in the ranking system is another step of the method. The method further includes placing each evaluation category at a location on the circumference of the closed curvilinear graph. The steps of the method also include providing the evaluation categories and ranking system to an entity being evaluated. The entity selects a rank in response in each respective category according to the method. Plotting the ranking of each respective category as a node in the closed curvilinear graph in response to the ranking by the entity is another step in the method.

In various embodiments of this aspect of the invention, the closed curvilinear graph is circular, spherical, arcuate, polygonal, and ellipsoidal and combinations thereof. In one embodiment, the ranking is numerical. In another embodiment, an expectation value for any category is set between the highest and lowest ranking for the evaluation category. In yet another embodiment, each node is in itself a closed curvilinear graph or SMT. In still another embodiment, each node is linked to its adjacent nodes. In another embodiment, each link between nodes is a directed link. In another embodiment, each directed link is associated with a respective value. In one embodiment, the respective value is a tensegrity factor. In various embodiments, the qualitative data is data about an entity, and/or an organization. In one embodiment, the qualitative data is ensemble data derived from a plurality of sources.

In another aspect, the invention relates to a method of qualitatively comparing the compatibility of two entities. The method further includes providing a plurality of evaluation categories and a respective ranking system. The method also includes the step of providing a closed curvilinear graph in which each unit of radius corresponds to a rank in the ranking system. Placing each evaluation category at a location on the circumference of the closed curvilinear graph is also part of the method. The method further includes providing the evaluation categories and ranking system to each entity. Having each entity select a rank in response in each respective category and plotting, for each respective entity, the ranking of each respective category as a node on the closed curvilinear graph in response to the ranking by the entity are also steps in this aspect of the invention.

In one embodiment of this aspect of the invention, the method further includes the step of determining the similarity between the plotted nodes. In various embodiments, the entities, include, but are not limited to, companies contemplating merger; individuals in an organization; individuals contemplating starting a company; a company and it proposed investors; and/or other suitable entities. However, it is to be understood that the SMT and the methods described herein are not limited to one set of entities or relationships. As such in other embodiments, suitable entities also include, but are not limited to, individual people, couples, families, communities, patients, counselors, doctors, clubs, and any group or collection of people about which information is available.

In yet another aspect, the invention relates to an apparatus for analyzing qualitative data. The apparatus includes a plurality of evaluation categories and a respective ranking system. A closed curvilinear graph in which each unit of radius corresponds to a rank in the ranking system with each of the plurality of evaluation categories being placed at a location on the circumference of the closed curvilinear graph is also included in the apparatus. The apparatus also includes an output device for providing the evaluation categories and ranking system to an entity being evaluated; an input device for having the entity select a rank in response in each respective category; and a display plotting the ranking of each respective category as a node in the closed curvilinear graph in response to the ranking by the entity.

In still another aspect, the invention relates to an apparatus for analyzing qualitative data. The apparatus includes means for providing a plurality of evaluation categories and a respective ranking system; means for providing a closed curvilinear graph in which each unit of radius corresponds to a rank in the ranking system; means for placing each evaluation category at a location on the circumference of the closed curvilinear graph; means for providing the evaluation categories and ranking system to an entity being evaluated; means for having the entity select a rank in response in each respective category; and means for plotting the ranking of each respective category as a node in the closed curvilinear graph in response to the ranking by the entity.

In yet another aspect, the techniques associated with the SMT include an overlay function. Specifically, once two or more SMTs have been generated they can be overlaid on a properly scaled curvilinear graph such that the categories are aligned as desired. This allows multiple entities to be compared at once and at a glance. For example, using the scheduling SMT outlined below, the schedules of multiple individuals can be stacked in an overlay format to discern any schedule conflicts or openings. The overlay feature of the SMT has many broad applications and in fact can be applied whenever two or more SMTs exist.

Although the term "spherical" in the SMT is used to convey the circular or spherical nature of the data representational format, the term The Sphere and spherical are also used to refer to a larger set of ideas, constructs, and relationships. As used herein, in part, The Sphere is a succinct designation to represent any system users choose to model and wish to understand. The Sphere can comprise networks of interconnected nodes. In turn, some of the component nodes may also be SMTs themselves.

In one embodiment, The Sphere and the SMT are at least one of the following: multinodal, interconnected, tensegral, interdependent, self-organizing, aware, nascent and attractive. In one embodiment, the SMT is used to indicate conformity to or deviations from parameters defined within a spherical model, a circular model, or other model incorporating a curvilinear graph of plotted nodes.

In one aspect, the SMT is multinodal. Additionally, SMTs enable whole system evaluation using multiple nodes and/or multiple SMTs. The nodes are interconnected in various embodiments. In The Sphere and suitable SMTs nodes can represent, but are not limited to, people, ideas, projects, teams, communities, data, information, business entities, organizations, other SMTS, tensegrity values and/or any entity that comprises a sphere of activity.

In one embodiment, the interconnections between the nodes are associated with a particular tensegrity value indicative of the magnitude of the tensegral relationship between the nodes. In some embodiments, the tensegral relationship is direction specific. In one embodiment, tensegrity is the dynamic force at work in every interaction. Tensegrity is modeled in some aspects and embodiments of the SMT.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
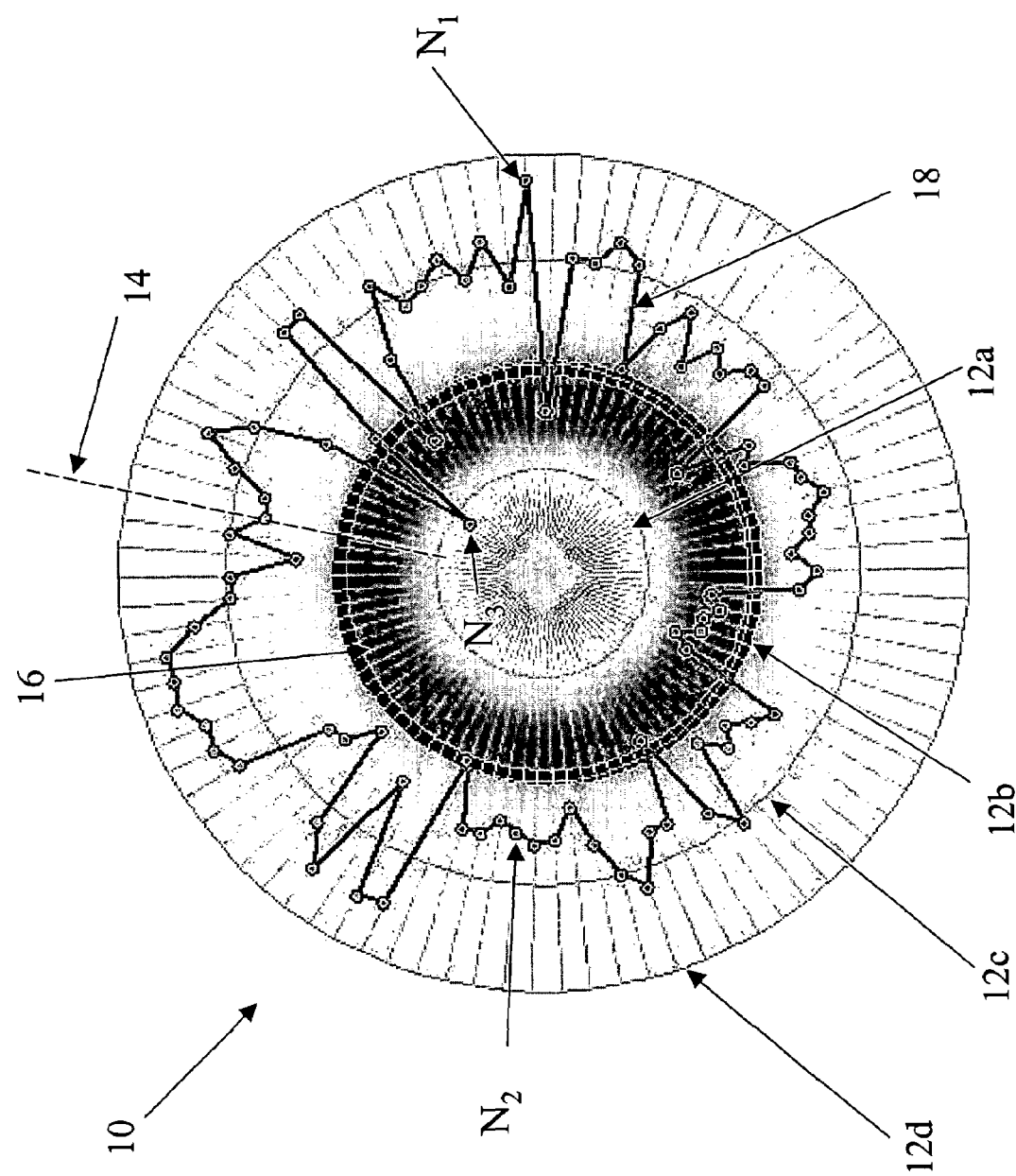
FIG. 1 is an exemplary SMT according to an illustrative embodiment of the invention.

The presently preferred and alternative embodiments of the invention, including the best mode for practicing the invention known at this time, are now described in detail in connection with the accompanying drawings. It is, however, expressly noted that the present invention is not limited to these embodiments, but rather the intention is that modifications that are apparent to the person skilled in the art and equivalents thereof are also included.

The Spherical Modeling Tool is a modeling tool that creates a visual representation of the dynamics of virtually any system or activity. The SMT is applicable to an infinite range of data and systems, including, but not limited to, individual lives, physical health, organizations, projects, communities and community activities, political systems, social institutions and global systems of all sorts. The SMT provides valuable and useful insights into the interconnected, interdependent workings of the system being modeled. Accordingly, the SMT based approaches disclosed herein are particularly suitable for awareness, assessment, development and decision support models. The graphical nature of the SMT makes understanding and interpreting the results fast and easy.

The methods and apparatus of the Spherical Modeling Tool disclosed herein generally relate to various multidimensional modeling platforms and techniques for organizing information using circular or spherical arrangements. Although the term, Spherical Modeling Tool (SMT), is used throughout the document, the SMT encompasses two dimensional, i.e. circular, and multi-dimensional, i.e. spherical or hyper-spherical, modeling techniques. The implementation of the modeling techniques, the SMT templates, the SMT software, and the apparatus used in their respective implementations are also within the scope of the SMT.

As discussed above, an aspect of the SMT relates to creating visual representations of data and relationships. Specifically, the SMT is suitable for producing various types of graphs, plots, overlays, templates, three-dimensional surfaces, and animations representing changes between the same. These visual representations include, but are not limited to various circular, arcuate, polygonal, star, spherical, and/or curvilinear two-dimensional graphs or three-dimensional surfaces or solids. In one embodiment, a graph paper (or other suitable media) comprising concentric visual representations as discussed above is used to generate the SMT. However, in other embodiments, a computer, cellphone, and/or a PDA, is used to generate the visual representation. Once the visual presentation has been generated and the relevant nodes plotted, in some embodiments, some or all of the underlying ranks and curvilinear segments can be removed such that some or all of the pattern of connected nodes is all that remains visible.

In one embodiment, the methods associated with the SMT are implemented using one or more computer programs. The programs are computer or PDA based and can be used by a standalone program, a network, or made available on the Internet. As a standalone program, the SMT can be used by a single user, when made available via the Web or other computer networks the SMT can be a shared multi-user program. Specific embodiments of the SMT can be coded as specific modules designed to operate within existing graphical design and mathematical processing packages such as AutoCAD (Autodesk, Inc., San Rafael, Calif. 94903), Maple (Maplesoft, Waterloo, Ontario, Canada), Mathematica (Wolfram Research, Inc., Champaign, Ill.), MatLab, (The MathWorks, Inc., Crystal Glen Office Centre, Novi, Mich.), Microsoft Excel, Microsoft Outlook (Microsoft Corporation, Redmond, Wash.) and other suitable software suites. Alternatively, the methods and approaches of the SMT are also suitable for use by individuals or organizations using electronic or manual approaches to complete pre-made templates according to the embodiments discussed below.

The SMT is used to visualize the whole or targeted subsystems of a particular system. One characteristic of the SMT is its use of shape as a means for analysis and evaluation. In contrast with standard data visualization tools, the SMT allows the user to incorporate both subjective and objective data simultaneously. It provides a method for visualizing the shape of a system in relation to the goals or expectations of the user. As such, introducing the SMT is readily accomplished via an illustrative figure.

FIG. 1 illustrates some of the general terminology and concepts associated with the SMT. Specifically, FIG. 1 shows an exemplary SMT representation 10. The SMT shown could be manually prepared by a user or automatically generated in response to a particular data set via a software or firmware implementation. The SMT allows for the simultaneous viewing of any system by multiple data sources plotted on the circumference of the sphere or circle as nodes. FIG. 1 shows four concentric circles 12a, 12b, 12c, and 12d corresponding to specific levels or ranks within a model formulated according to the principles of the SMT. Although each circle corresponds to a given rank, an infinite number of ranking gradations are possible in between and to either side of a given circle in the representation 10. As shown, the SMT depicts the interrelationships of the data points (nodes) as patterns plotted on a graph (curvilinear plot).

Returning to FIG. 1, various nodes are shown in the figure with nodes $N_1$, $N_2$, and $N_3$, specifically designated. The nodes intersect various radially distributed categories at specifically selected positions. An exemplary category is shown by the dotted radius portion 14. While each radius corresponds to a particular category or user directed question, movement along a given radius reveals changing gradations of value associated with the ranking for that particular category. Thus, a particular SMT might be formulated to evaluate a worker's overall job satisfaction and the category associated with radius 14 might correspond to salary level satisfaction. In turn, the particular radial value of the nodal position would indicate the employee's specific satisfaction level for that category.

In the exemplary model shown in FIG. 1, node $N_1$ corresponds to the highest ranking value for the dataset illustrated. While node $N_2$ represents an average ranking value clustered near several other similar ranks for different categories. Node $N_3$ corresponds to the lowest ranked category value. A specific ranking level known as the expectation level is shown as the dark circle 16. User expectation levels are discussed in more detail below.

Accordingly, as user or system variables are ascribed to different nodal values for different radial categories, a graphical representation is built up that reveals a model of an individual or the overall system. These SMT based plots can be compared to other models or a representative spherical or circular paradigm.

The overall pattern of the SMT model shown in FIG. 1 is shown by connecting the nodes with straight or curved line segments. The resultant closed curve 18 is shown as a visual representation of a given user or system's valuation of a predetermined class of categories. If portions of a SMT correspond to a user's expectation level, some harmonics exist. However, if there are deviations from a user's expectation level, some discordance exists. Accordingly, one or more SMT based models can be used to depict data relationships in terms of harmonics and/or discordance. The SMTs of different users can also be compared to assess levels of similarity given the comparative levels of harmony and discord in overlapping or different parts of their respective SMTs.

When viewing multiple source plots for the SMT the user can instantly see where there are harmonics in the SMT. These appear where nodes, sectors (groups of categories) or areas of the SMT trend the same or similar. Conversely, the user can instantly see areas of discordance via the SMT when seeing nodes, sectors or areas of the SMT where the plots significantly diverge, or become discordant.

Figure 2:
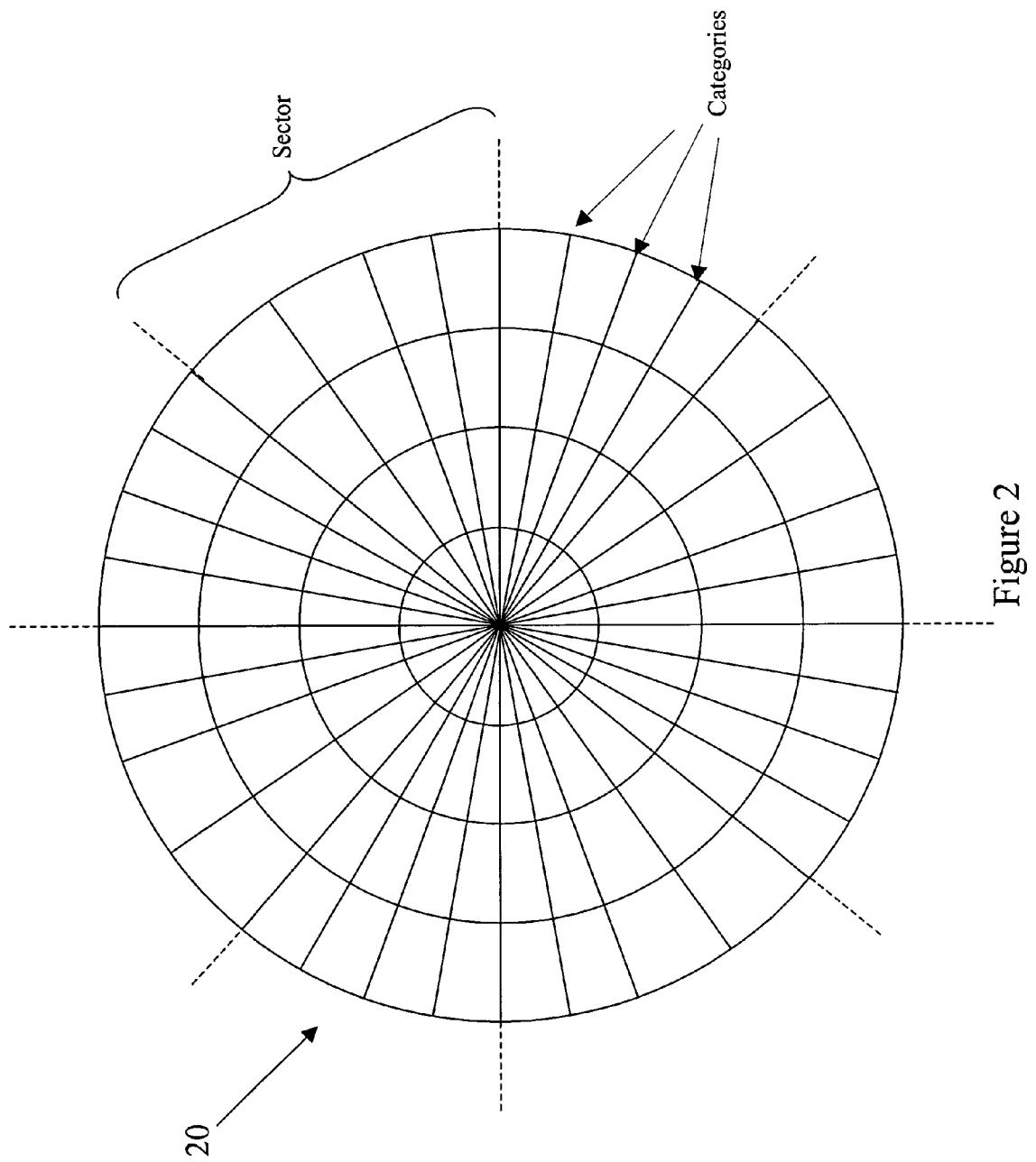
FIG. 2 is an exemplary template suitable for modeling and recording data according to the teachings of the invention.

Since the SMT graphically depicts how changes or alterations in a system impact all other system elements, useful easily understood models can be quickly obtained. In some implementations, the SMT can be generated by a user positioning and connecting nodes on a blank SMT modeling template 20 as shown in FIG. 2. Once a SMT 10 is finalized, such as in FIG. 1, it can be critiqued and compared to those of different users. With numerical data entry or click-and-drag techniques and an SMT software implementation, users of the SMT see an instant representation of the spherical shape of the system as well as the dynamics that shape it. Thus, SMTs are particularly suitable for, but not limited to, seminars, teambuilding exercises, company evaluation, and personnel feedback.

Figure 3A:
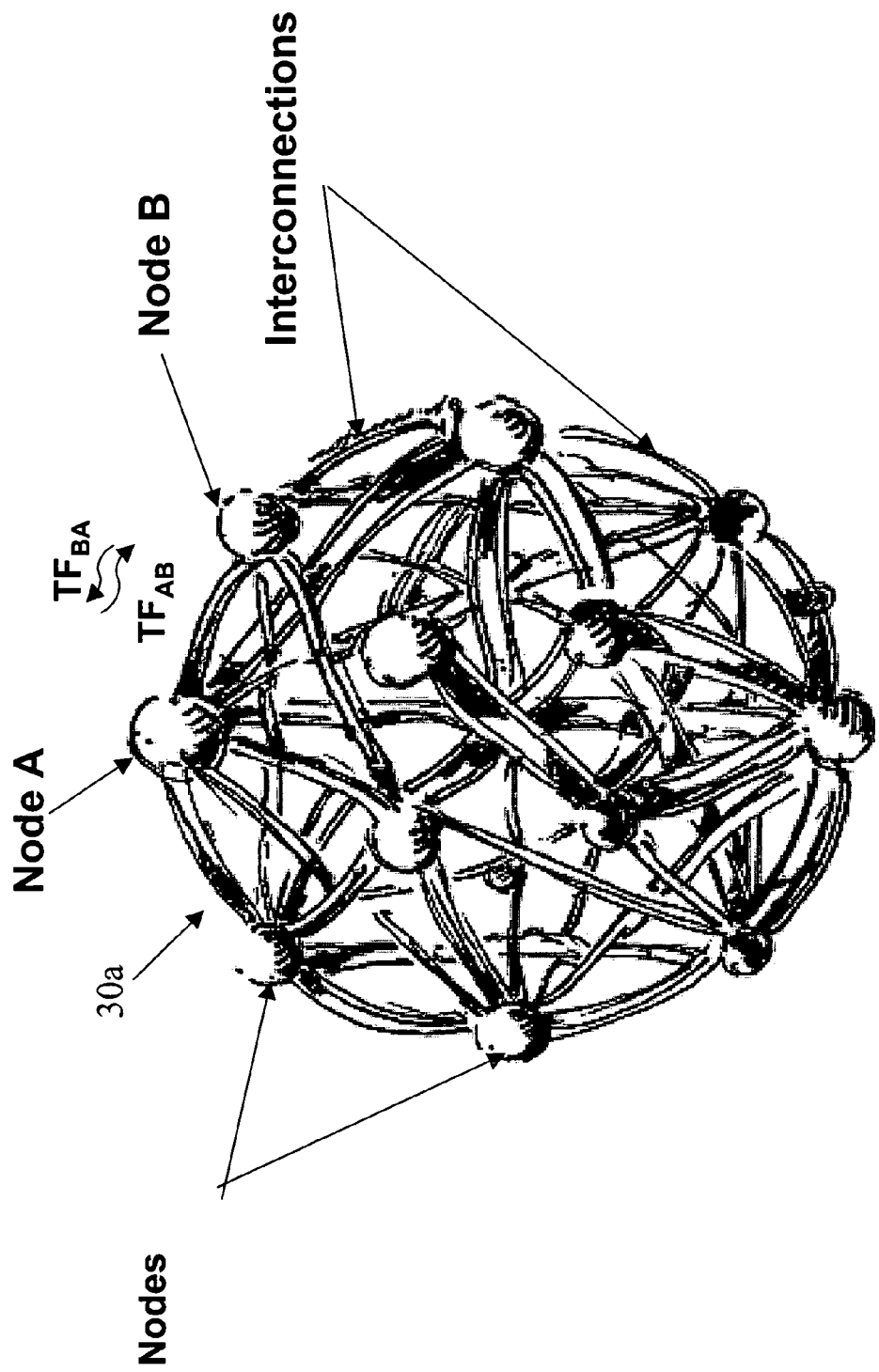
FIGS. 3A-3C are perspective views of a stylized sphere made up of nodes and interconnections that depicts a multi-dimensional system embodiment of the invention.
Figure 3C:
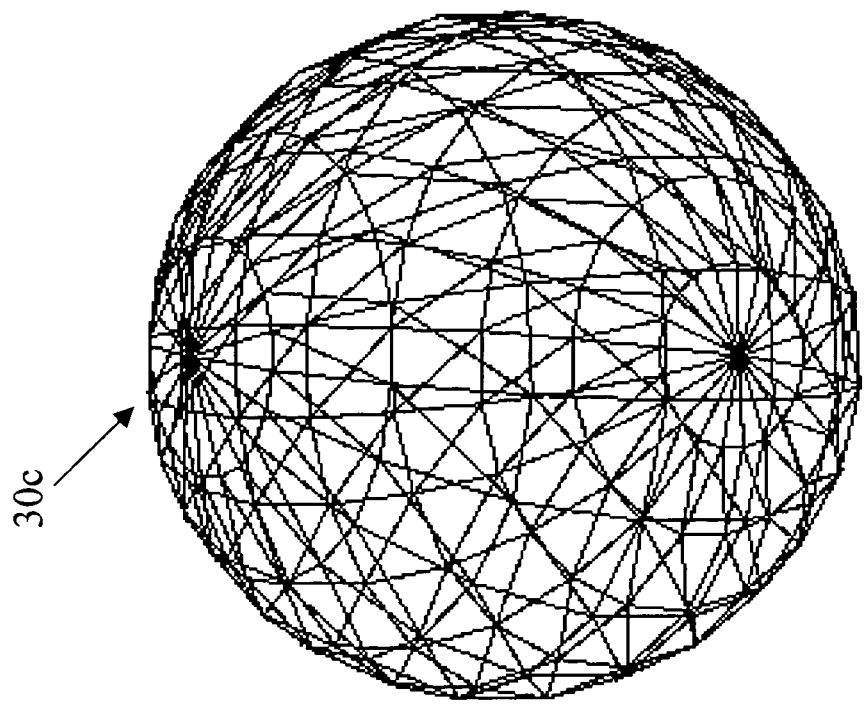
Figure 3B:
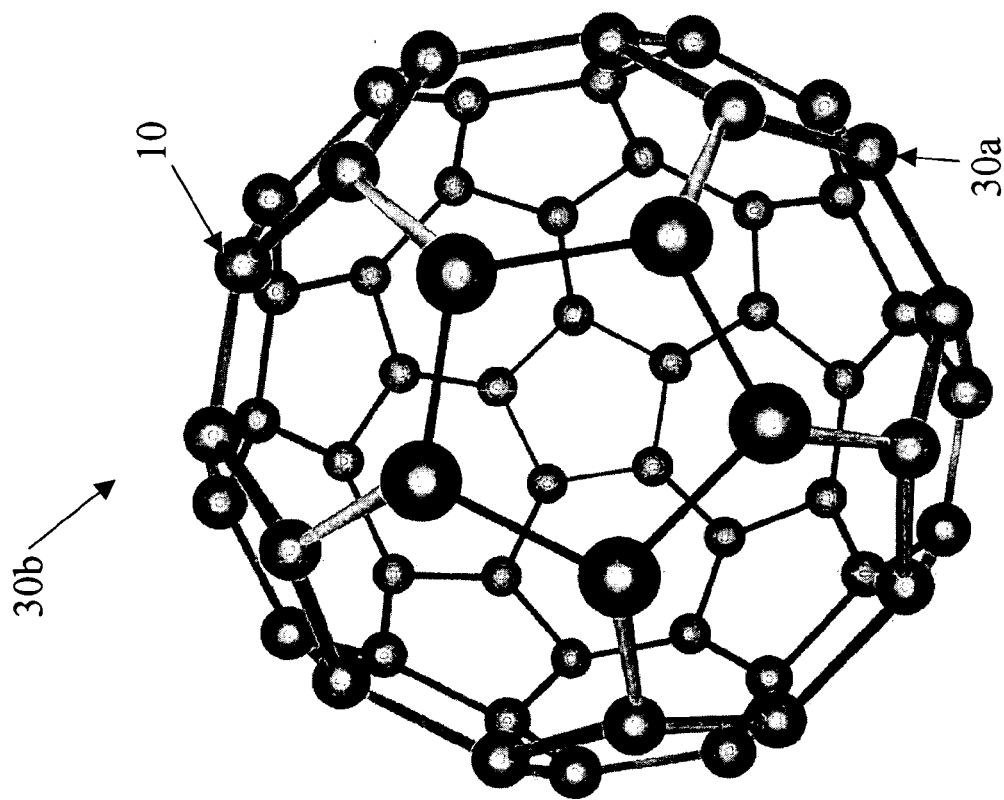

The SMT models the shape of systems based on data input for each node. FIG. 3A, shows a three-dimensional representation of a SMT 30$a$ with a plurality of nodes and nodal interconnections. The position of each node on the circle or sphere is determined by plotting each node. In one embodiment, nodes are plotted on a 0 to 10 scale, in 0.1 increments. However, various scales and ranking values can be used without limitation. FIG. 3A also illustrates the expansive and elastic nature of the SMT. Although a plurality of interconnected nodes populate the SMT 30$a$ of FIG. 3A, it is possible in one embodiment for each node to also be an SMT. This concept can be further extended with the SMT 30$a$ of FIG. 3A and the SMT 10 of FIG. 1 corresponding to nodes in a still larger universal SMT 30$b$ as shown in FIG. 3B.

In other embodiments, the SMT may be implemented using a spherical representation. In such a representation, the concentric circles of FIG. 1 would be replaced by nested spherical shells such as that shown in FIG. 3C. Although a wireframe SMT 30$c$ is shown solid surfaces are also possible. While the connected planar curvilinear plot could be represented as an appropriately deformed closed three-dimensional solid or surface. Similarly, the overall view of the spherical embodiment would be achieved using perspective drawing techniques, two dimensional cross-sectional views, and/or a revolvable spherical computer representation.

The numerical value of the node is determined by the user or facilitator based on the expectation of where that node should be. The midway point on the exemplary SMT scale introduced above, the 5 position, represents the point at which the user would "expect" the node to be. If the node value is exceeding expectation it is rated above 5 (See for example, $N_1$ in FIG. 1). If it is below expectation it is rated less than 5 (See for example, $N_3$ in FIG. 1).

The expectation point or level on the SMT can be shown with a thicker dark line that represents the halfway point on the scale used for the SMT. This is the point of expectation for each node on the sphere. The dark line approach was used in FIG. 1. However, other graphical approaches can be used to indicate the expectation level.

For example, in an SMT based model depicting a person's health or wellness, one of the nodes they would likely be rating is weight. If the user's current weight is where they expect it to be they would move the weight node to rank 5 using our exemplary radial ranking scale. If they feel they are overweight, they place the node above the 5 rank. Conversely, if they determine their weight is low then they will rate the weight node below a 5.

The SMT does not make nor provide judgments about good or bad, right or wrong valuations. An above 5 positioning for a node does not necessarily mean positive or good. A low rating number does not mean negative, or bad. The SMT simply reflects the perceived and/or actual reality of a node in relation to expectation as determined by the user. The judgments, evaluations and analyses are those of the user, not the modeling tool.

There are some exceptions to plotting the SMT scale based on expectations. In some embodiments, the scale may be used to indicate a preference between two choices. An example of this can be seen in a personality test based SMT that questions a person's natural inclination toward being an introvert or extrovert. In this embodiment, the user positions the node to reflect if they are more introverted (below the 5 position) or more extroverted (above the 5 position). The final position of the node is a reflection of how much of an introvert or extrovert the person feels they are. Thus, the SMT can represent a continuum of values between two polar extremes, rather than only rank radial categories. Also, the scale used for evaluation of expectations is not restricted to 0 through 10. It can be also be a plot of percentages of a whole. Or it can be any mathematical equation that generates data that could be displayed on a scale of any number to any number.

In part, the SMT incorporates techniques to impart additional information to the link between the nodes. Characterizing the omni-directional energy and relational parameters existing between interdependent nodes via the interconnecting links is desirable in some embodiments. The interactions and relationships between nodes related to the concept of tensegrity. Tensegrity is a term proper to architecture that refers to the dynamic tension and integrity of structures. Tensegrity, as it is applied to Sphericity and the SMT, refers to the omni-directional push/pull energy of the connections between nodes in a system.

Some SMT examples are not always suited for showing the tensegrity between the nodes and its impact on the overall shape of the SMT. The tensegrity is what gives structural integrity to the shape of the SMT. The more cohesive and integral the connecting links between nodes, the greater the integrity of the system. However, tensegrity can be depicted using other approaches in some embodiments.

Two-dimensional and multi-dimensional SMTs can be used as described above with great benefit without the incorporation of tensegrity. In other embodiments of the SMT, the model can be created as outlined herein but can also incorporate the ability to demonstrate the tensegral relationship (tensegrity factor) between all nodes and the resulting sphere or SMT.

The tensegrity factor is a numerical designation, or algorithm using a 0 to 10 scale in increments of 0.1 to represent the impact of one node on another node. However, other scales and increments can be used without limitation. Unlike the nodal positioning on the SMT, wherein most embodiments the position of 5 represents expectation, there is no standard or expected number for the tensegrity factor.

While somewhat analogous to weighting parameters in some mathematical formulas, the tensegrity factor (TF) is unique. In some embodiments the TF can be a common numerical TF between one node and all other nodes. In other embodiments, the TF will be common from one sector of nodes on the SMT to all other sectors of nodes. Or the TF may be unique between sectors. In some embodiments, the TF will be unique from one node to each and every node on the SMT.

Furthermore, it is noteworthy that the TF is bi-directional. This is illustrated in FIG. 3A. The TF from node A to node B ($TF_{AB}$) may be rated at a 7.2, but the TF from node B to node A ($TF_{BA}$) could be a 1.3. However, the interplay of TF values can be shown in various methods, by thicker or differently patterned connectors, numerical labels, and other suitable manual and computer based approaches.

The concept of TFs can be better understood via a straightforward business example. If the president of a company is shown in the position of node A and the janitor is node B, the impact of their work on each on the other is not the same. If the president does not do his job properly and hence endangers the company the impact of his failure is far greater on the janitor than the impact on the president by the failure of the janitor to properly do his job. This is shown by the different TFs, a 7.2 from node A, the president, to node B, the janitor. When indicating the janitor's impact on the president we see the TF is a 1.3. In this example, the bi-directional TF would clearly be very different between the president node and the node representing the CFO, as it would be with almost all employees in a small firm.

Tensegrity factors can also be shown as categories in an SMT such that the overall SMT reflects the TF interaction and relationship between the entities shown in the SMT. Thus, as the TF changes the SMT can change over time. The TF can also be shown in a SMT by changing the relative position of a given node as affected by the TF from another node, i.e. CEO's embezzlements impact on the node of the janitor who loses his pension. These two SMTs can be shown wherein the nodal position changes as a function of TF or alternatively nodes can be shown in shadow or dotted lines to indicate their former or future position based upon TF induced changes.

The TF values are unique to each organization and subjective. In one embodiment, a master TF matrix is created in the form of a look-up table to provide pre-designated TFs between designated sectors and/or nodes for an organization. TF look-up tables can be then applied to any organization (personal or project) SMT allowing a quick and easy way for the user to realize the added value of the TF function. The user can then modify the TF values in the look-up to more accurately reflect their organization or for use in 'what if' scenarios.

The TF between sectors/nodes can also be assigned by a user or by an algorithm. TF master look-up tables can also be assembled by behavioral scientist, psychologist, organizational development specialist and others. Although TF inclusion is applicable to only certain SMT embodiments, the need to generate data to formulate TFs and the overall SMT remains necessary for all embodiments.

Data for plotting the node position on the SMT can originate from any number of sources. In one embodiment, the node position is selected by at least one of a single user, multiple users, survey respondents, and/or through the dynamic generation of data. Thus, one person can complete a form or respond to a questionnaire. The resultant data can be input manually or automatically. Data entry can be carried out by an individual user or a third party. There is no limit as to the number of people involved in rating the nodes. Data generated by multiple respondents can be displayed and arranged by individual respondent or by groups of respondents.

Moreover, SMTs can be generated automatically from databases and be updated in real time. For example, in a company SMT the profit node could be updated from the profit and loss (P&L) by setting an expectation for the profitability of the company. If the expectation set was that profit was to be 10% of revenue, a 10% profit would be plotted as a 5. If the P&L showed profit was at 15% this would automatically be plotted above a 5. The same procedures would be used to plot cash flow, sales, lead generation, and productivity and so on. This approach allows company executives to visualize the shape (condition) of their company in real time via a company Intranet based SMT.

Figure 4:
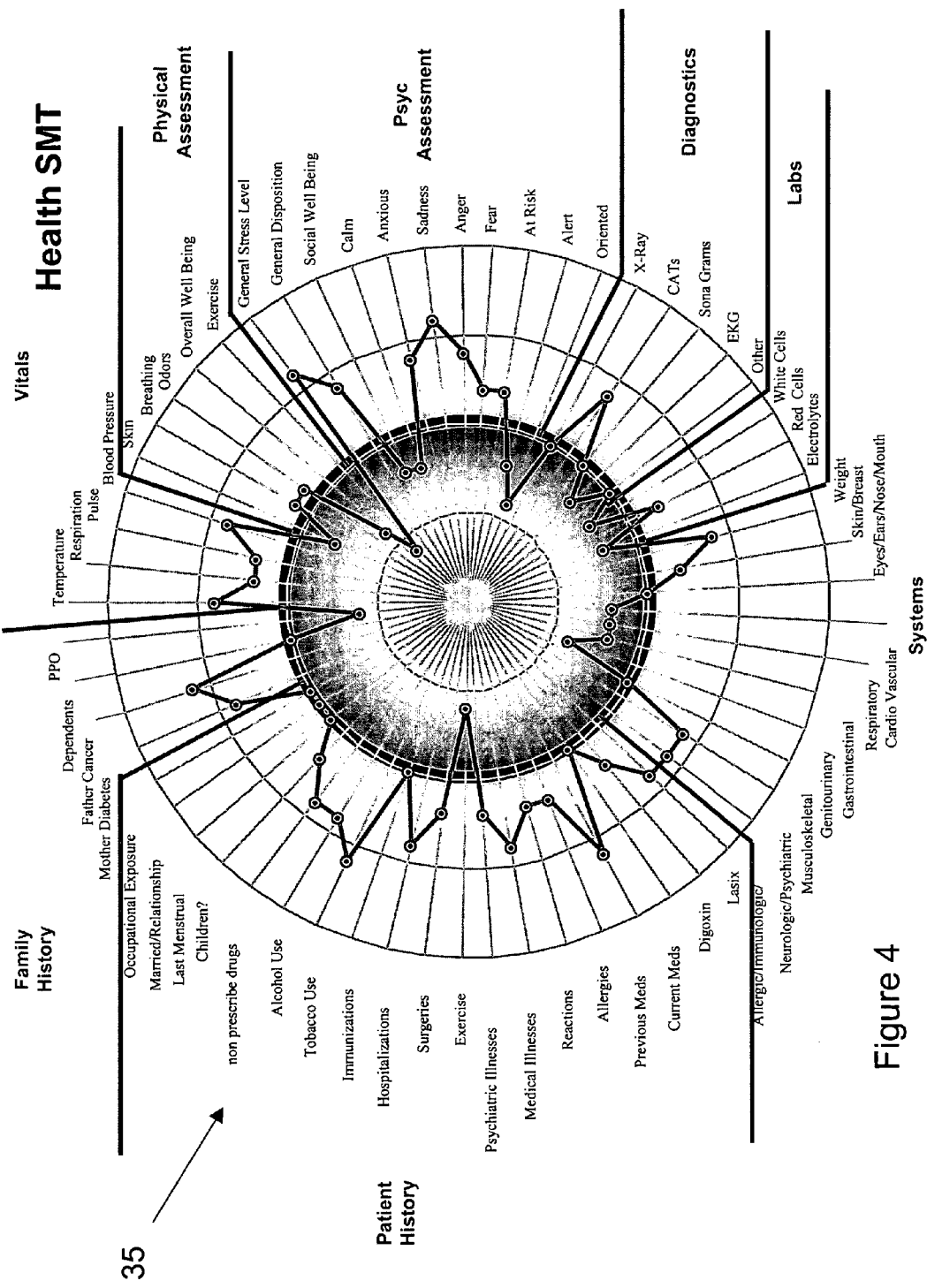
FIG. 4 is an exemplary SMT relating to health and medical issues according to an illustrative embodiment of the invention.

The integration of various data generation and acquisition approaches can be seen in a simple example of a health SMT also referred to herein as a health sphere. An exemplary health SMT 35 is shown in FIG. 4.

This SMT 35 is designed to show a spherical snapshot of a patient's overall health. The Health SMT instantly shows the entire sphere of the person, allowing quick visualization of interconnected interdependence of all factors impacting the patient's condition. The Health SMT conveys a quick comprehensive snapshot of the person's overall health, allowing patterns between nodes to be seen.

Nodes on the SMT are grouped in sectors as units of radius on the sphere. In some embodiments, sectors comprise a grouping of interrelated nodes. For example, in the health SMT 35 there are sectors for nodes dealing with physical issues—blood pressure, pulse, RBC count—and there can be sectors such as medications, finances or emotional condition.

Many variations of the Health SMT are possible. Each can be customized and used for many different specific applications. In one embodiment, all special health SMTs are sectors on a primary patient SMT which would be updated automatically with any new treatments and available to all of the patient's health care providers.

The patient Health SMT 35 shown in FIG. 4 includes the following sectors: patient history, family history, vitals, physical assessment, psychological assessment, diagnostics, labs, systems, and meds. The health SMT will be different for each person in that there are some nodes that will apply to some people, but not apply to others.

The subject of the SMT 35 has a family history of both diabetes and cancer, rates their overall well being low, very little exercise, high stress level, are anxious, sad, have anger, fear and are considered at risk. The patient is currently using two meds (Digoxin and Lasix), and has used a lot of medications in the past. Also, the patient is suffering from some allergies and is a heavy user of tobacco is overweight and has some serious issues as visible in the systems sector.

The source of data for this example arises from one or more medical patients. New patients generally fill out a form to provide the medical provider an overview of their condition and/or complaints. This information can be displayed as a SMT which itself will become a sector on a larger patient SMT. The medical staff provides additional information with regard to vitals, physical assessment, medications etc., which can be fed to the original patient sphere as a sector. To provide a health baseline, data can be pulled from outside medical databases to serve as a nodal point of comparison. Finally, the nodal data on the SMT can be applied to a mathematical algorithm to identify specific risk for the patient, such as medications that should not be used, and so on.

While one feature of the SMT is to show as many nodes of information as possible on the primary SMT, display limitations can make it difficult if not impossible to show all nodes at one time. In other embodiments, it may be possible to physically display all nodal data but there are times when specific data is better viewed separately. For these reasons, in one embodiment a SMT implementation has a function known as Spheres within Spheres in which all nodes and all sectors can themselves be displayed as SMTs or spheres.

The Spheres within Spheres function can be used when there is a need or desire to look at a specific sector of information as a sphere separate from the primary SMT. Using the Spheres within Spheres function, the primary SMT's sectors are plotted and displayed as individual spheres, but linked to the parent sphere. The secondary spheres nest inside the main SMT. Any number of spheres can be nested one within another depending on the evaluation and analysis needs of the user. FIGS. 3A-3C illustrate aspects of this concept in a three-dimensional embodiment. However, the spheres within spheres feature also extends to two-dimensional circular SMTs.

Using the Spheres within Spheres function, the user is also able to click on (or otherwise access) any node on either a primary SMT or a nested SMT, and see all the elements that compose that node displayed as a separate SMT. Alternatively, this data can also be displayed as textual information.

The data plot display is in the shape of a sphere, either two dimensional or multi-dimensional. If there is only one user supplying individual data, the SMT simply plots the data. In many embodiments there will be multiple people and or sources supplying data for the SMT (there is no limit to the number of people or sources that could supply data to the SMT). When there are multiple sources of data the plot can be depicted via multiple views.

To get a snapshot of the shape generated, all source data can be consolidated so that there is only one plot line on the sphere. The data can also be displayed as multiple plot lines consolidated from the separate sources. The SMT can also display individual source plots.

The overall consolidated SMT plot lines provide a way to see the overall shape (person, organization, project etc.). The multinodality of the SMT and its ability to simultaneously display objective and subjective data makes this view useful in increasing the awareness of the whole and its internal/ external interconnected interdependence.

In addition to the SMT's unique ability to meaningfully display large amounts of diverse data, the SMT has the ability to simultaneously view multiple sources for the data, either by group or individually. This can be done by overlaying one or more SMTs. As a result, the curvilinear plots for different users stack and can be viewed simultaneously.

SMT overlays can be used for evaluation of any type of relationships, including business partnerships, employee hiring and even dating. A Mate Finder SMT, for example, would assist people to find compatible partners. A Dating SMT would overlay the SMTs of prospective partners to evaluate matches. The process would be far faster, easier, less costly and more effective than current services. An alternative approach would allow people to model their ideal partner and then search the services archives for matches.

The business equivalent of the dating SMT is to be found in assisting companies with executive searches and employee hiring. By overlaying a company SMT with the SMT of job candidates, companies could more quickly and effectively search for and find compatible members.

Overlaying SMTs can also be used to compare and match two or more different organizations or companies to discover potential harmonics or discordance. This capability could be used in assessing joint ventures and would be invaluable in assessing potential mergers and/or acquisitions. The SMT is unique in its ability to simultaneously create a visualization of both objective and subjective issues and by overlaying the SMTs of companies considering a merger, acquisition or joint venture to detect the potential for a harmonic or discordant relationships.

As different users and systems generate different SMT shapes, it becomes apparent that the shape of a given SMT is meaningful and conveys specific information. Thus, there is significance to the resulting shapes and patterns created with the SMT. The shapes and patterns provide instant insights into the condition of and/or unique traits of the person, activity or organization being modeled.

If all nodes are at expectation the resulting shape would be that of a sphere or circle. Although rare, this shape indicates a person, organization or activity that is at expectation on all nodes of evaluation. This spherical condition is both desirable in some embodiments.

If a large portion of the nodes were below the expectation point, an imploded shape results that represents a person, organization or activity that was in distress. The more imploded the overall shape the more critical the problems.

If a large portion of the nodes were above the expectation point, an expanded shape indicating a person, organization or activity that is doing very well beyond expectation results. The more expanded and spherical the overall shape, the more extreme the situation. Extreme situations can be a positive sign for the entity or an indication of danger or risk. In one embodiment, the SMT is used as a tool to bring awareness, however, characterizing an entity as good or bad is not its chief objective. By providing an unbiased assessment of an entity, the SMT allows the entity and others to be aware of what is going on so that further analysis can be undertaken and changes made where appropriate and possible. In its role as a diagnostic tool, the SMT presents information, but does not attempt to judge the subject entity.

In situations where the nodes did not trend together in being at, above or below expectation but were plotted all across the scale the resulting shape would indicated a person, organization or activity that is in turmoil.

Some of these features and geometries can be understood through an exemplary SMT. Specifically, these features are present in the Leadership SMTs shown in FIGS. 5A-5C. The Leadership SMT provides a way to see our life in a manner that we can identify our unique leadership abilities. In particular, it allows us to very quickly and effectively see our unique leadership. By showing the interrelationship between many seemingly unconnected aspects of our life, patterns emerges that help us better understand our leadership skills. By seeing the emerging pattern of our leadership we can evaluate our natural leadership abilities and take any actions we determine appropriate to enhance our leadership.

Figure 5A:
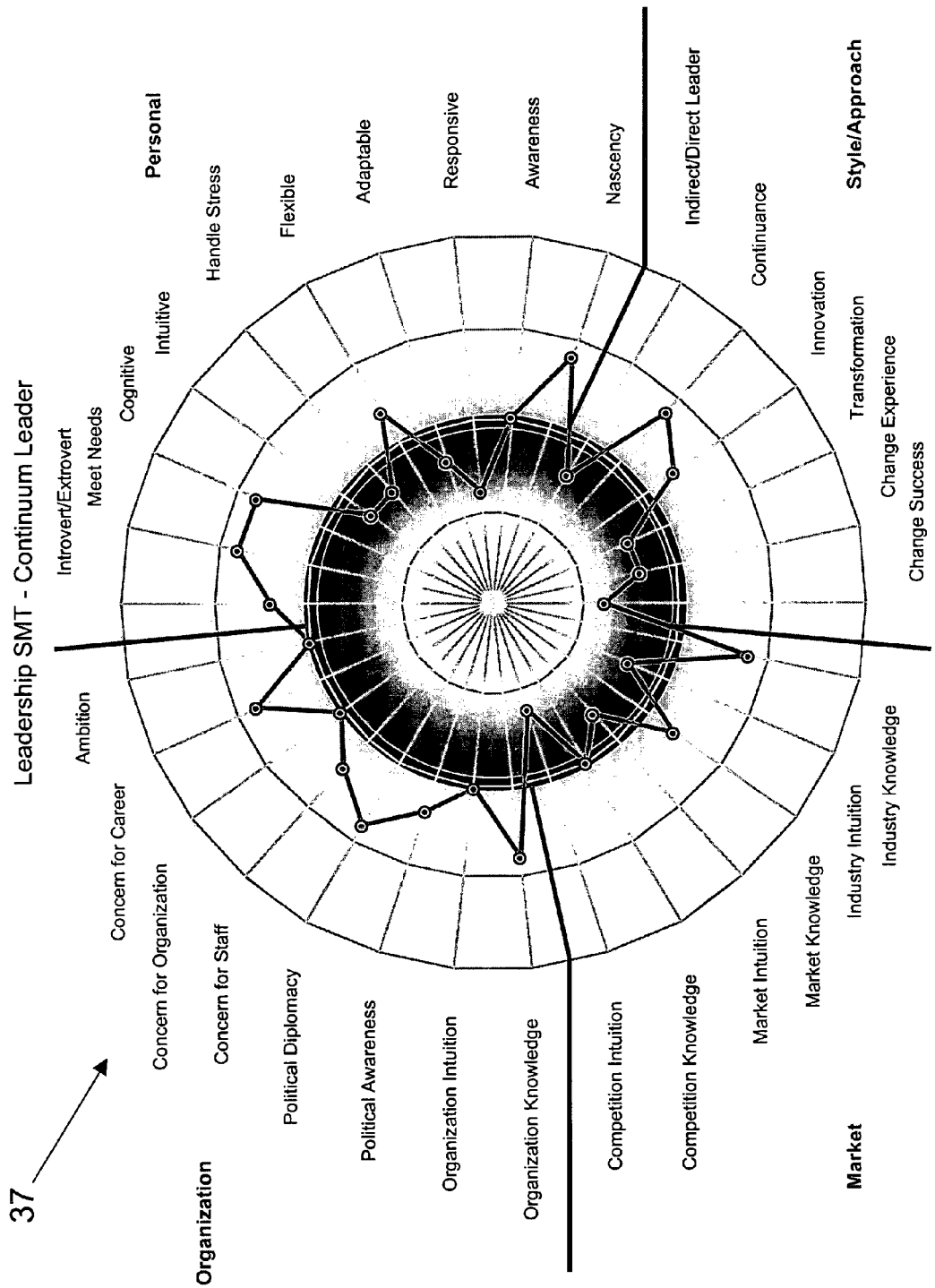
FIGS. 5A-5C are exemplary SMTs depicting different leadership styles according to an illustrative embodiment of the invention.

As shown in FIG. 5A, a continuum leader's shape is the most spherical of the three leadership styles shown. It is the job of a continuum leader to successfully maintain the company and/or project, but not to make radical or significant changes. With this SMT 37, the more spherical the leader's shape the more of a continuum leader they will be.

Figure 5B:
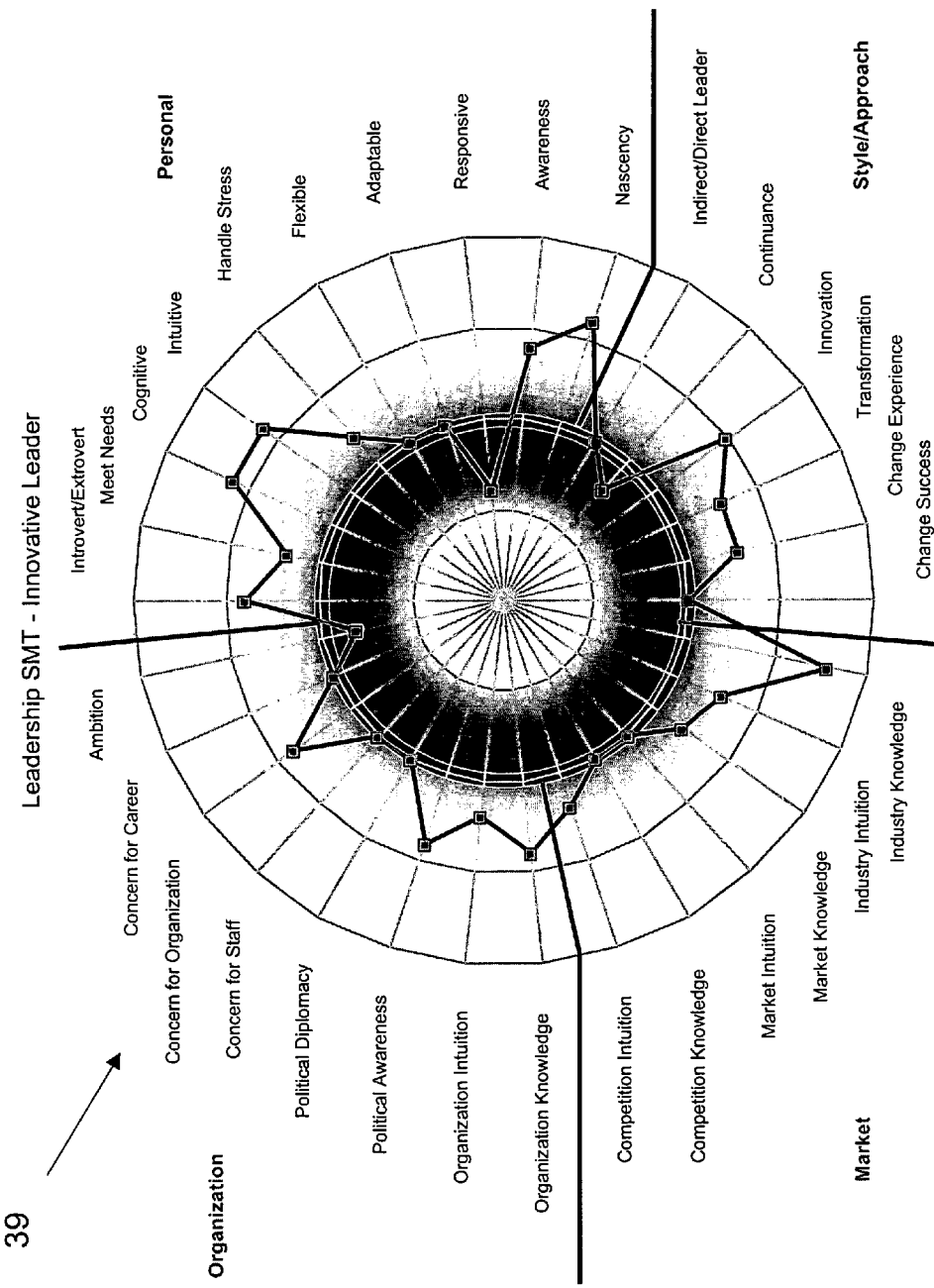

FIG. 5B, shows an SMT 39 for an innovative leader. An innovative leader is one who is supposed to change things, come up with new approaches to doing current activities. Innovative leaders will show a distinct pattern in rating some areas higher above expectation than a continuum leader, as well as other areas that will be rated below the continuum leader's ratings. The resulting pattern will show somewhat above expectation in flexibility, adaptability, responsiveness and innovation as well as a lower rating on continuum activities. This pattern will visually communicate that the person is more innovative.

Figure 5C:
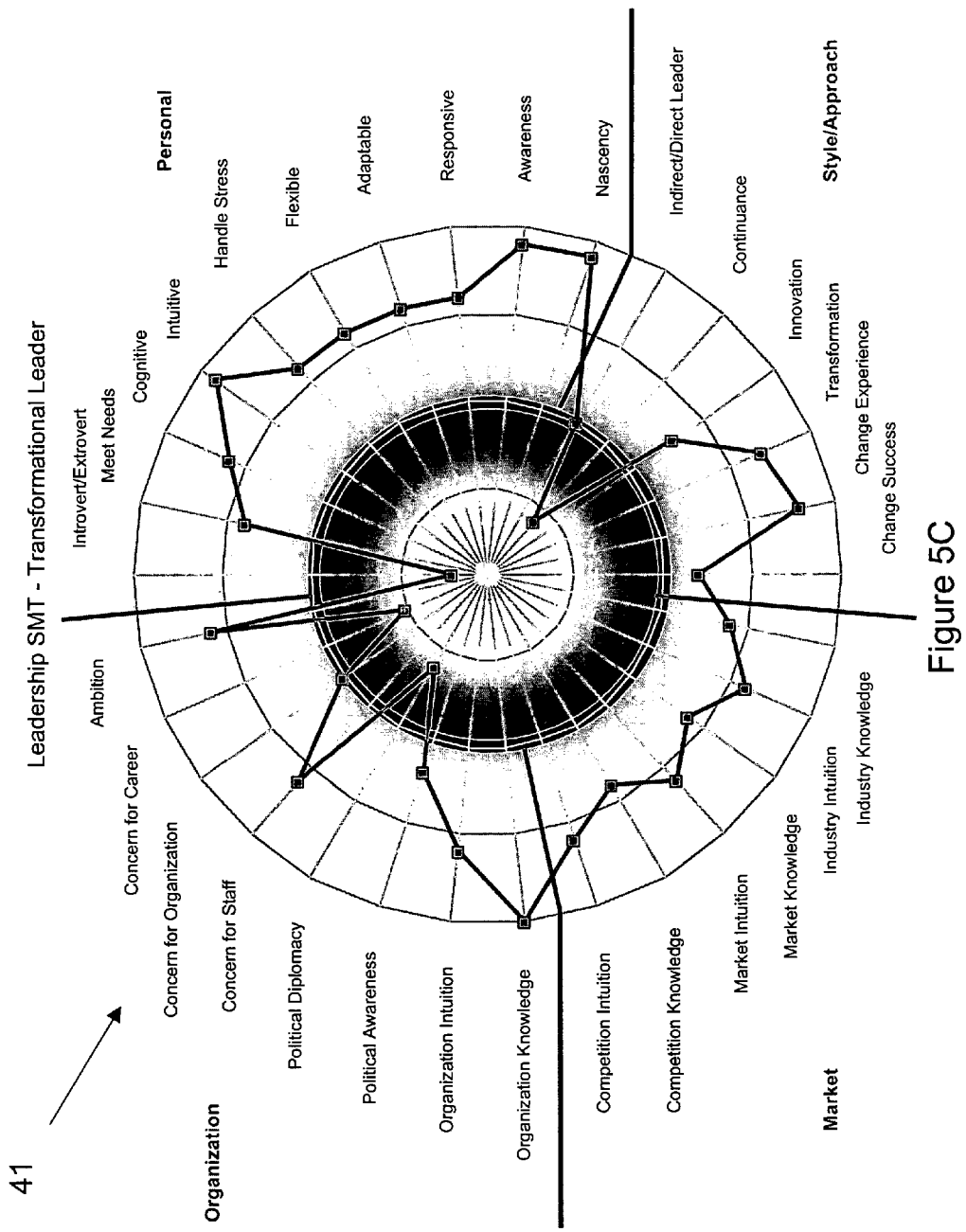

In one embodiment, the transformation leader's pattern will be the most radical of the group. An SMT 41 for transformational leader is shown in FIG. 5C. Transformational leaders are rare and they are instantly recognized by their SMT pattern. A transformation leader's job is to transform, to do this they must be extremely flexible, adaptable, responsive, with extensive change experience. At the same time they are not detail oriented and are generally not as politically sensitive. The resulting pattern will be by far the most extreme, showing very high ratings on some nodes and very low on others, with few nodes plotted at expectation. As such, the pattern for a transformational leader will be instantly recognizable.

The SMT can be used to model and evaluate virtually any system or system component. The SMT models the whole (a person, activity, organization, community or the world) showing both objective and subjective data plotted onto a sphere (closed curvilinear graph or surface plot) as nodes where there is meaning in the resulting shape and manifest patterns. The SMT allows the user to visualize the interconnected and interdependent relationships between the nodes, or areas of activity, as well as showing the relationship between individual nodes and the entire sphere.

The resulting shapes and patterns aid users to visualize the interconnections and interdependencies of all nodes on each other and on the whole sphere providing a dramatic increase in accurate awareness and appropriate action. The SMT graphically depicts how changes or alterations in any aspects of the organization impact all other elements.

Multiple user perspectives are shown by multiple individual and/or group data response plotting on the sphere, the resulting shapes and patterns showing harmonics, discordance or polarization in perspectives.

A SMT can be a phase state snapshot showing the shape at the time of modeling. Or the SMT can be dynamic showing the ongoing metamorphosing of the shape when its inputs are real time data. This dynamic capability of the SMT is further enhanced because nodes can be added or deleted from the modeling program as needed. Thus, some exemplary SMTs are interactive allowing users to model 'what ifs' by moving nodes and seeing the resulting shape.

Unlike many modeling approaches in which data is rolled up to provide consolidated reports, the SMT shapes increase in accuracy, insights and value as more nodes are plotted on the sphere. This feature allows users to compare, contrast and evaluate whatever data influences the overall shape of the system.

Nodes in the SMT represent the elemental and indispensable aspects that make up the spheres of individual lives, organizations and societies. The SMT is unique in its ability to meaningfully and simultaneously display both objective as well as subjective information in the form of nodes on the SMT.

For example the SMT can display hard data for a company such as profit/loss, cash flow, sales revenue as well as provide a way to rate a company's strategy, operational procedures and employee attitudes. It allows executives, investors, managers and others in the organization to see data in a meaningful context displayed in a single model.

Unlike typical analysis charts and graphs that consolidate data into the fewest number of elements, the SMT is designed to visualize the objective and subjective data in context at any desired level of granularity. Its unique design allows users to compare, contrast and evaluate whatever data influences the overall shape of the system.

For example, a typical bar chart showing profit or loss provides little understanding about which aspects of a business contributes to the profit or loss. A pie chart that shows the portion of budget used by various departments does not provide any way of ascertaining the value of each department's contribution to the overall organization.

In contrast, an organizational SMT is capable of depicting profit/loss while at the same time showing the portion of budget used by departments and showing both objective and subjective data to reflect the contribution each department makes to the organization. The organizational SMT can show the current state of the national and/or regional economy (the larger system) as well as how competitors are current fairing in the market, and so on.

While initial data to create a SMT will generally come from data input as described earlier in this document, as a matter of physical operation, the SMT can also be manipulated with click-and-drag techniques for a graphic user interface (GUI) implementation. When viewing the SMT on an interactive display device, either some form of a computer or a proprietary display device, the user is able to click on any node and move it to a new or different scale position.

This click-and-drag ability allows the user(s) to run scenarios that visualize and analyze the effect of changing the position of a node or multiple nodes. This is not unlike the 'what if' function on a spreadsheet except that the SMT allows for the simultaneous modeling of both subjective and objective data. The SMT, in providing a graphical display of all elements and their interconnections, allows the user to visualize the impact of any number of changes on the whole system.

For example, the board of a fast-growing company believes that the company has outgrown its visionary founder and it is time to bring in an outside seasoned executive to take over. Before making a decision the board could commission a comprehensive SMT of the company, paying close attention to the TF between the founding visionary leader of the company and its employees, suppliers, investors and customers, as well as R&D, product development and other areas of the company.

With this tensegrity-enabled SMT the board could do a series of 'what ifs' in which the results of each scenario are instantly visualized in the SMT. The users could, for example, visualize the impact of terminating the current leader of the org and compare the resulting shape with the alternative of bringing in a secondary manger or of creating a new position for the founding leader where he is happy and his strong tensegral relationships continue to be an asset instead of being converted into a liability.

The same scenario-based use of the SMT is applicable to any planning or awareness process in which the user(s) need to make decisions based on multiple variables. It is as applicable to personal decisions, political decisions or community decisions as it is to business planning.

The features and the scope of the invention can be further understood by considering various examples. In various embodiments, these examples relate to specific method and system embodiments. In one embodiment, the methods and systems are implemented using SMT templates.

However, the methods and systems described herein can also be performed in software on general purpose computers, servers, or other processors, with appropriate magnetic, optical or other storage that is part of the computer or server or connected thereto, such as with a bus. The processes can also be carried out in whole or in part in a combination of hardware and software, such as with application specific integrated circuits. Suitable software can include JAVA, the C family, Visual Basic, pseudo code, machine language, assembly language, object oriented languages and others as known to those of skill in the art. The software can be stored in one or more computers, servers, or other appropriate devices, and can also be kept on a removable storage media, such as a magnetic or optical disks.

EXAMPLES

Although the following examples describe various two dimensional models, the examples are only included to show some of the SMT's characteristics described and claimed herein. The following examples are illustrative and not intended to be limiting. SMTs can be generated to handle any data set, whether quantitative or qualitative. Although, many SMTs described herein relate to expectation based data, scientific, statistical, and other data can also be represented using various scales and configurations.

The Education Assessment SMT

Figure 6:
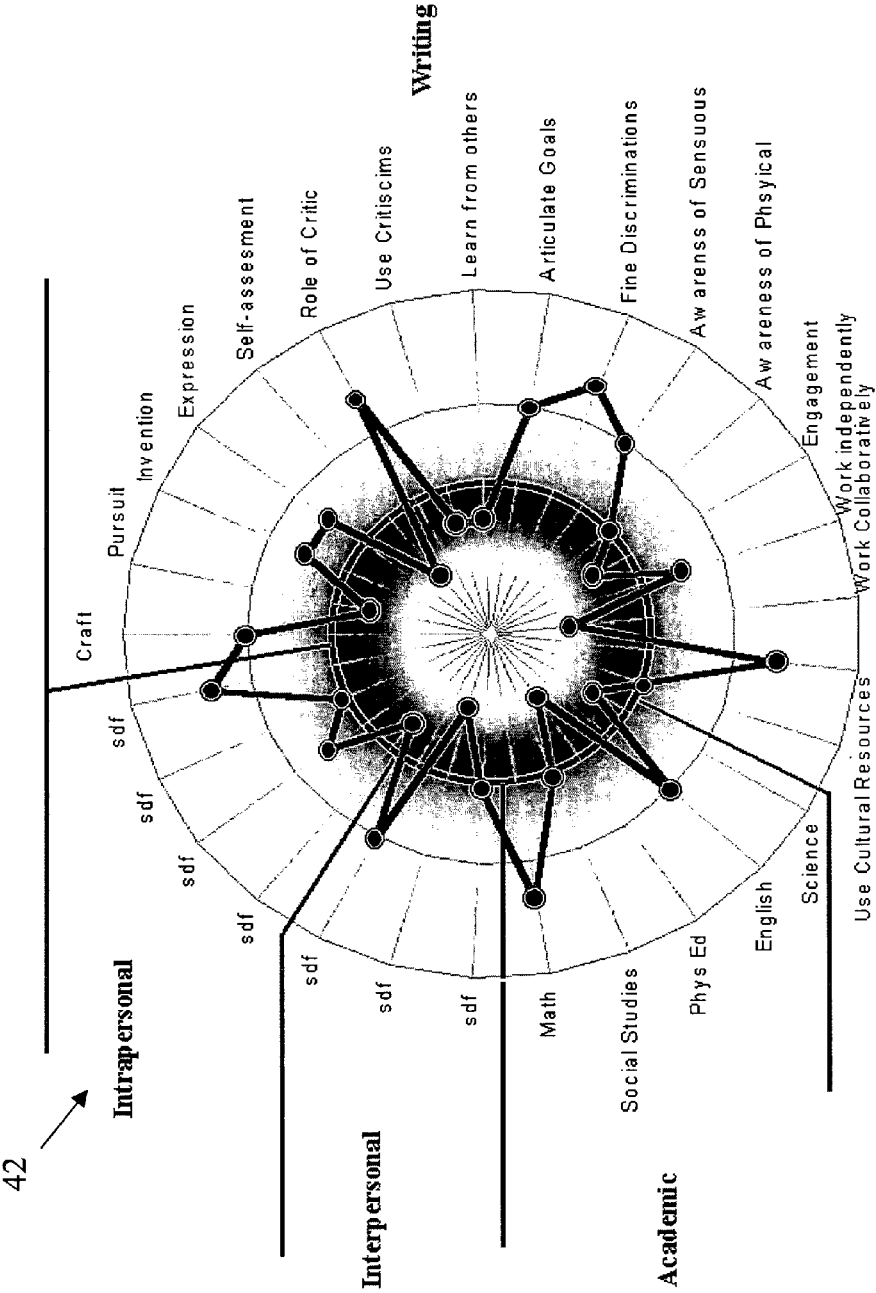
FIG. 6 is an exemplary SMT depicting an evaluation of a student according to an illustrative embodiment of the invention.

The SMT 42 can be extended to the educational environment. The SMT 42 shown in FIG. 6 represents a new approach for assessing students. Traditionally, students are evaluated on a standard alpha rating system, usually from an A to an F. This reporting system provides no insights into why a student rated the grade. It cannot show other factors that came into play positively or negatively impacting the grade.

Even more importantly, this reporting system provides no means to recognize and assess other qualities the student may have not in the standard reporting criteria.

The Education Assessment SMT 42 provides a means for instructors convey insights about those factors that impacted a particular grade or grading period. It also illuminates areas of potential and/or weakness of which the student and their parents should be aware.

But even more importantly, the Education Assessment SMT 42 allows for the student to assess themselves and overlay this with the teachers assessment. The Education Assessment SMT 42 can even allow multiple teacher plot overlays as well as other students who may be working on teams to plot how well the student it doing.

The Education Assessment SMT 42 shown in FIG. 6, has been designed for use with a student who is majoring in creative writing. As such, creative writing is not evaluated on a simple alpha, pass-do OK-do good scale. Instead, the elemental nodes that make up a creative writer have been identified so the student can be assessed on each of these. In addition to creative writing the student is still assessed on all other subject matter they are studying. Each of these other subjects can be explored in more detail with multiple nodes as has been done in the creative writing sector.

The Personal SMT

The Personal SMT allows a person for the first time in their life to see the whole of their life. A person can start to see the tensegral impact on their life of many aspects that they previously considered unrelated. The impact of the Personal SMT on a person can be profound.

The Personal SMT can show the whole of a person's life on one chart where interrelationships can be seen and contemplated. The personal SMT is ideally suited for use by counselors, personal coaches, psychologist, psychiatrist and others.

A master template of questions can be used as a starting point for every person to answer when preparing a personal SMT. But for some people entire sectors will be added or deleted as they apply to that individuals life. Each person will have custom nodes that will allow the Personal SMT to more accurately reflect the reality of their life.

Figure 7:
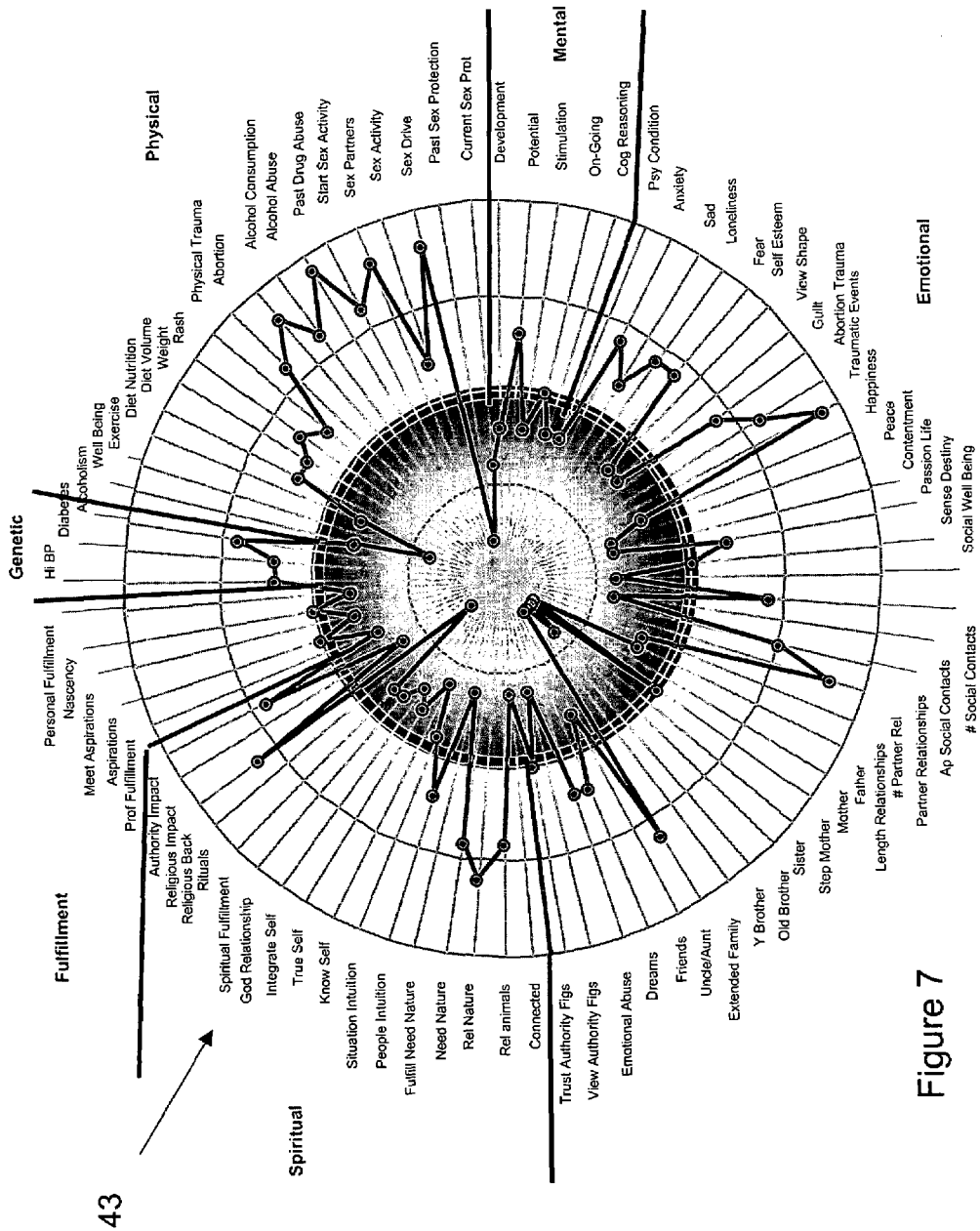
FIG. 7 is an exemplary SMT depicting aspects of an individual's life according to an illustrative embodiment of the invention.

An exemplary personal SMT is shown in FIG. 7. The subject of the SMT 43 is a person who is at risk and in need of immediate aid. The spiritual sector of the client's SMT 43 is severely collapsed. In the emotional sector we see virtually no contact with mother or siblings and recognition of emotional abuse. We also see this person has experienced an extremely traumatic event.

In the physical sector we see heavy alcohol abuse and current consumption. A very high level of past drug abuse. The subject has a family history of high blood pressure, diabetes and alcohol abuse. While this person indicates they are not at peace or very happy and they have a great deal of stress and are anxious, we also see very strong support from the immediate family as well as a strong spiritual connection to nature and animals that provides some support.

Genetically this person has a family history of cancer, diabetes, heart trouble and depression. The client's physical sector is very telling, no exercise, poor diet, surgeries (13) significant pain and a whole array of medications.

The client believes they have very good cognitive, teaching and management abilities but their aspirations are not being met.

The Organizational SMT

For profit and non-profit organizations are facing unprecedented challenges in successfully running their organizations as the world and their fields change at an increasingly rapid pace. The Organization SMT provides the leaders of organizations with the ability to see the whole of their organization including their competition and any other external forces, in one single chart.

In seeing the whole, they can see how various nodes on their organizations can or are impacting other nodes/activities and they can respond appropriately to the real needs of the organization.

Figure 8A:
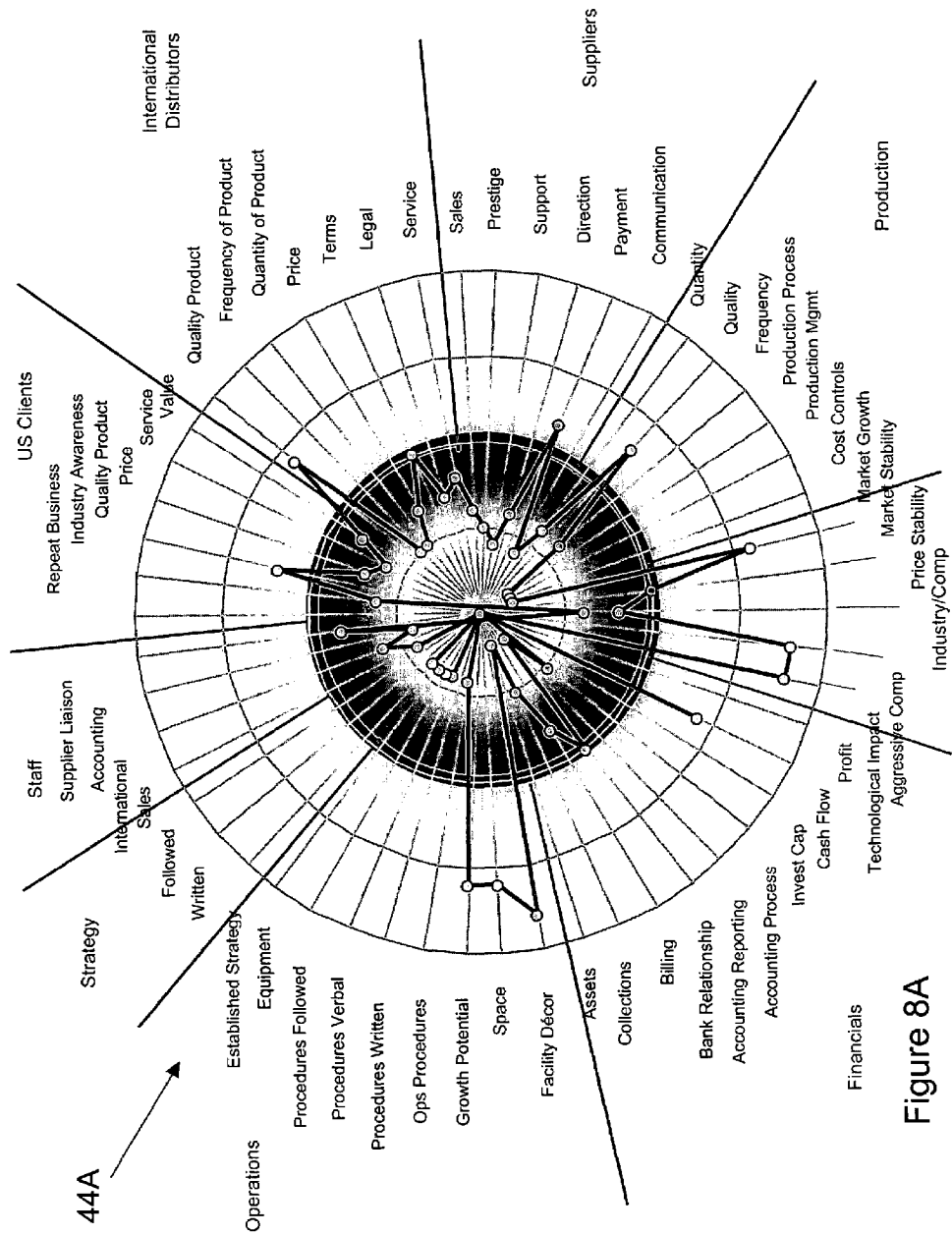
FIGS. 8A and 8B are exemplary SMTs depicting the state of a small company at different points in time according to an illustrative embodiment of the invention.
Figure 8B:
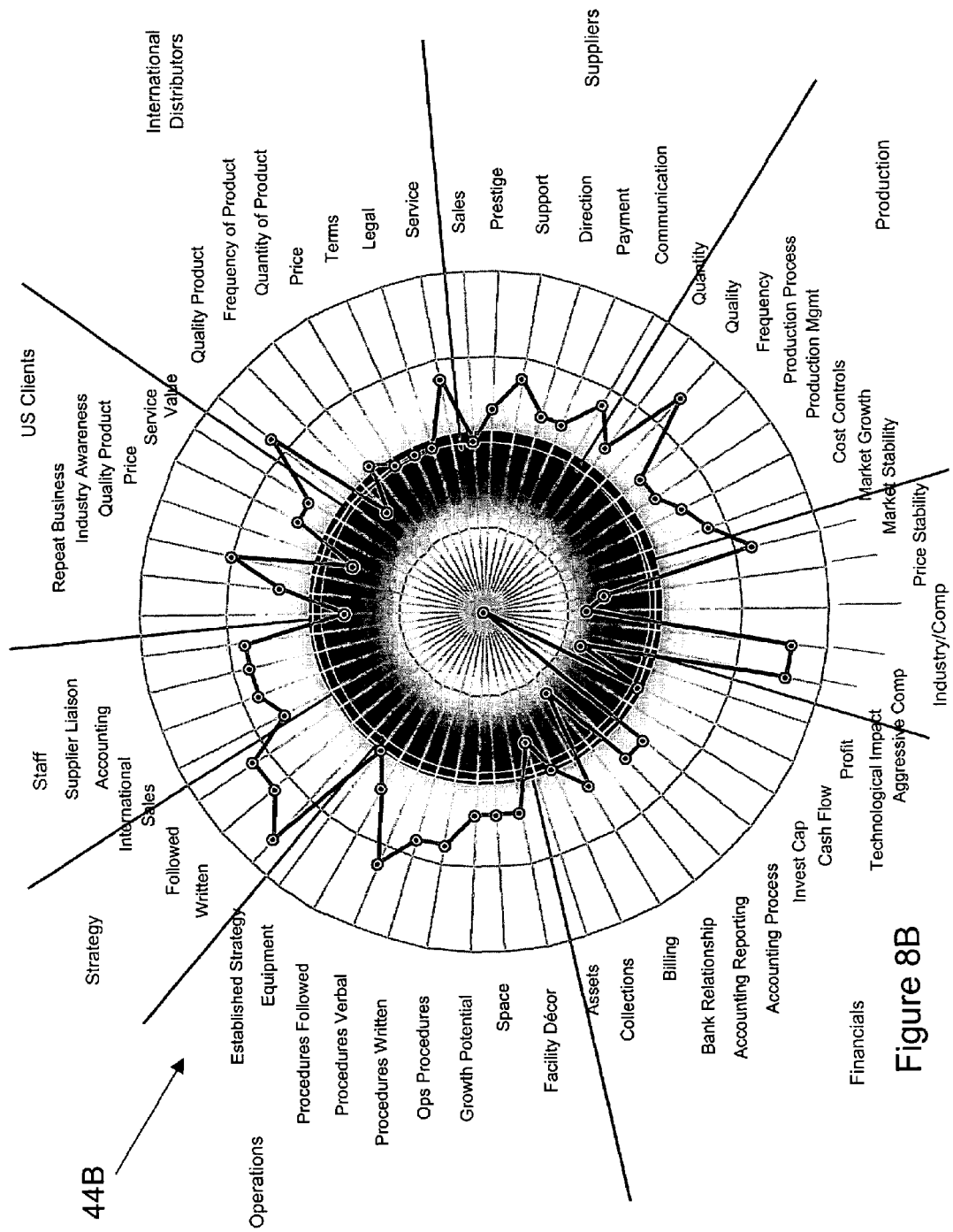

In the example SMTs in FIGS. 8A and 8B, a small manufacturing and international distribution company is evaluated. In FIG. 8A the company is in serious financial trouble. The second SMT in FIG. 8B shows the shape of the same company nearly 2 years later.

Turning to the SMT 44A in FIG. 8A reveals that this company is in serious financial trouble. In fact, the company has been loosing about $300 k per year for the past 2 years. In the financial sector this is evident in the lack of profit. There are only two points above expectation for this organization in the financial sector, cash flow is strong, and they have a good banking relationship.

The organization is a number of years old and has typically responded to any industry changes when it felt like it. It has no strategy in place. In the Industry/Competition sector we see the industry is growing while this company is not resulting in net loss of market share. The industry is also in a roll up phase as it has attracted the attention of large, well funded organizations outside the industry that see this as a growth industry.

Staff is not trained well. US customers are almost all one time customers who are not impressed with their products. Suppliers are not happy except that they are paid in a timely manner. International distribution is keeping the company alive. In their markets they feel the product is a good product at a very good price. Operationally and in production the company has no real procedures and is experiencing significant cost overruns.

Turning to the SMT 44B in FIG. 8B shows the same company less than 2 years later with new management. New management developed an effective strategy for the company, trained and/or replaced the staff as needed. Improved the quality of the product to meet US standards, improved the relations with international distributors. Met the needs of suppliers. Established and implemented production and operational procedures.

All of the foregoing was done out of cash flow. The new strategy changed a company that was quietly dying into a highly visible, competitive player with the potential for significant fast growth. The company was projecting growth in excess of 50% for the next year and prepared the staff and operations for this. Production costs were significantly decreased.

As is evident on the Organizational Sphere it did not have the capital to go it alone. The company had been positioned for external venture financing and/or sales of the business to the large organizations that were buying companies in the industry. The company was successfully sold.

Sales Department SMT

Figure 9:
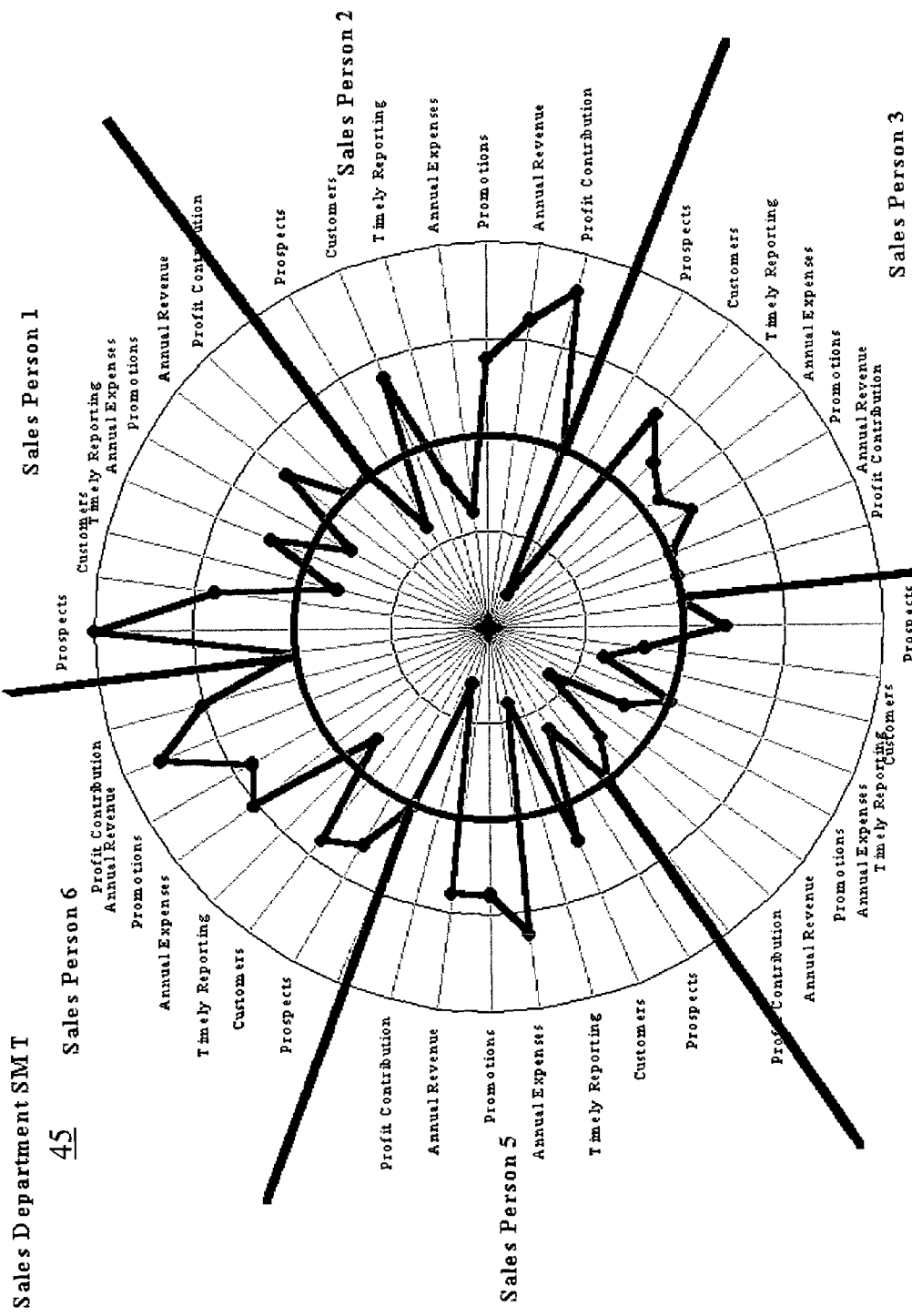
FIG. 9 is an exemplary SMT depicting a company's sales force according to an illustrative embodiment of the invention.

In FIG. 9, the concept of Spheres within Spheres is shown here in this Sales Department SMT 45. This SMT 45 is easy to read and instantly shows the overall shape of the sales department showing each sales person and how they were doing on seven key evaluation nodes.

Salesperson #1 is great at prospecting, keeps above expectation number of customers, expenses are a little high, revenue is good, profit contribution is at expectation. Salesperson #2 is not good at prospecting, keeps above expectation number of customers, keeps expenses below target, generates excellent revenue and even better great profit contribution. Getting Salesperson #1 and Salesperson #2 working together would be even better. Salesperson #3 is best at customer maintenance providing steady profit contribution. Salesperson #4 is below expectation in all areas and should be terminated. Salesperson #5 is dangerous to the org by his extremely high expenses (which may not even be accurate due to his slow reporting) which offset revenues leaving no profits. Salesperson #6 is good at prospecting and keeping customers. He or she is the best revenue generator and provides good profits to the organization.

The Project Analysis/Management SMT

Figure 10:
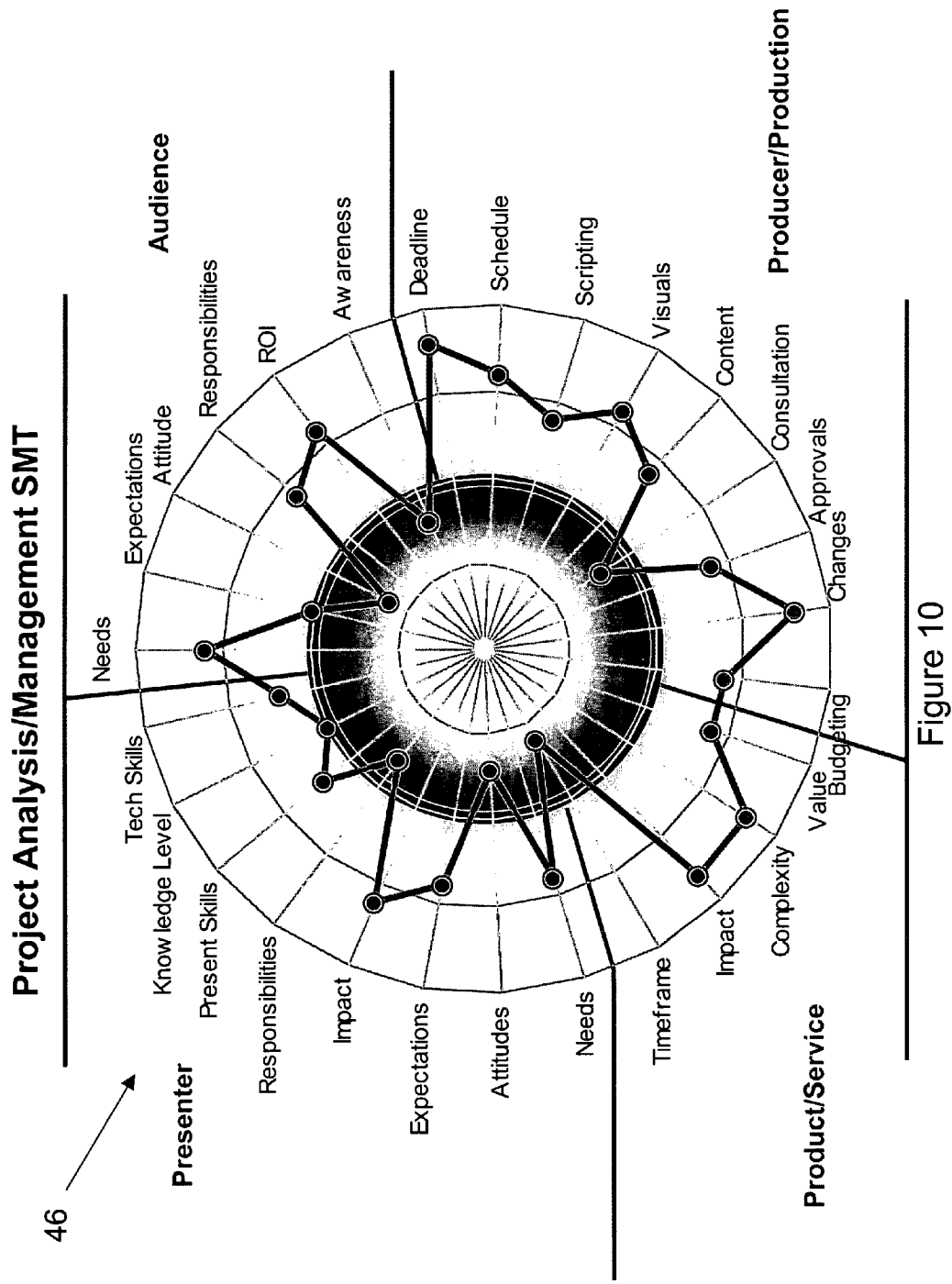
FIG. 10 is an exemplary project management SMT according to an illustrative embodiment of the invention.

The Project Analysis/Management SMT provides a way, at the conception of a project, to see all the elements that impact the success of a project. All Project Analysis/Management SMTs can be customized to the specific needs of the project at hand. As a pre-planning analysis tool they show the all elements, objective as well as subjective impacting the project. FIG. 10 shows an exemplary project analysis SMT 46.

As a project management tool, they have the ability to display the status of all elements impacting the successful completion of the project simultaneously. In showing all nodal elements impacting the successful completion of a project, the project manager as well as all project participants and executives can see the real-time status as well as potential problems with the project.

As a project management tool this SMT 46 is created by the separate input from all parties working on the project. Daily or weekly updates are posted by all parties showing on the 0 to 10 scale where they are in regard to expectation for that day/week. If they are at expectation, their node is a 5, behind schedule they rate the node less than 5 as appropriate and ahead of schedule above 5 as appropriate.

All parties working on the project as well as executives can access the Project Analysis/Management SMT via a secure Web site or Intranet site. In one embodiment, each node can be clicked on to show the sphere of that node. This is vital in helping all parties to understand why a node is behind or ahead of schedule.

This Project Analysis/Management SMT 46 shows a large new product presentation to be given to a major client. Parties impacting the success of this project include the presenter, the client and the producer/production team.

This SMT 46 helps all parties to see that the time frame to produce this presentation is short, the budget is slightly above average, though perhaps not enough due to the complexity of the project and the difficulty in getting consultations with product experts.

The product has the potential for significant ROI for the client who has a real need for the product though they have little awareness of their need for the product and hence are not excited as seen by their attitude node.

This SMT 46 quickly shows that this project is important to the presenter, his company and to the client. It is a complex product to describe, but one with significant potential value to the client. Time is very short, budget is marginal, access to the needed experts will be difficult and changes will be many and very time consuming.

The Schedule SMT

Time management is a booming industry in our increasingly fast paced world. Current time management systems continue to vainly attempt to break activities down into either linear line items or unrelated boxes of days of activities.

Using current time management systems to find out how busy one is during a given week or on a specific day requires reading nearly all of your entries to see your schedule. This is an extremely time consuming activity in itself, defeating the very concept of time management.

Figure 11A:
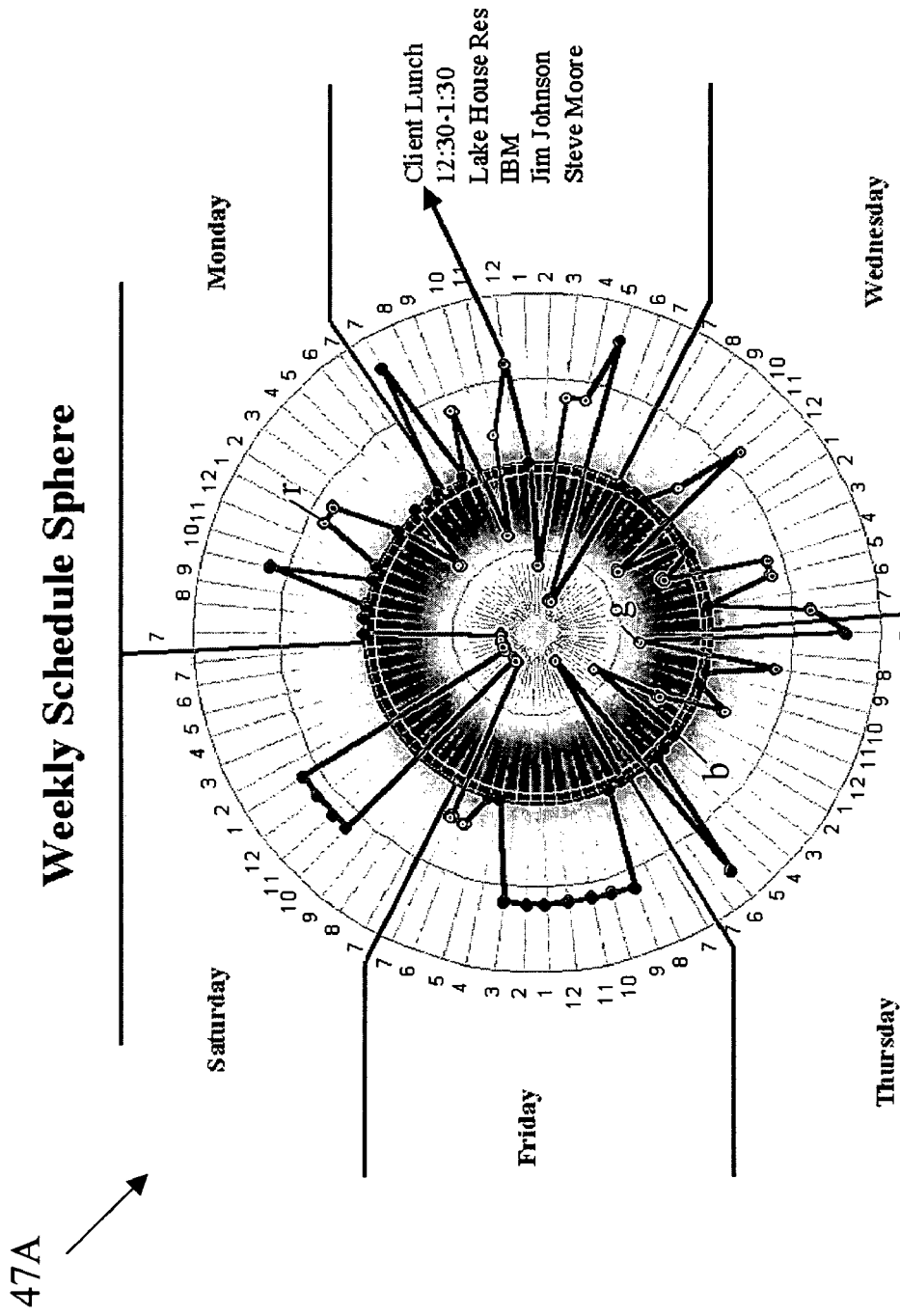
FIGS. 11A and 11B are exemplary SMTs depicting weekly and daily schedule SMTs respectively according to an illustrative embodiment of the invention.
Figure 11B:
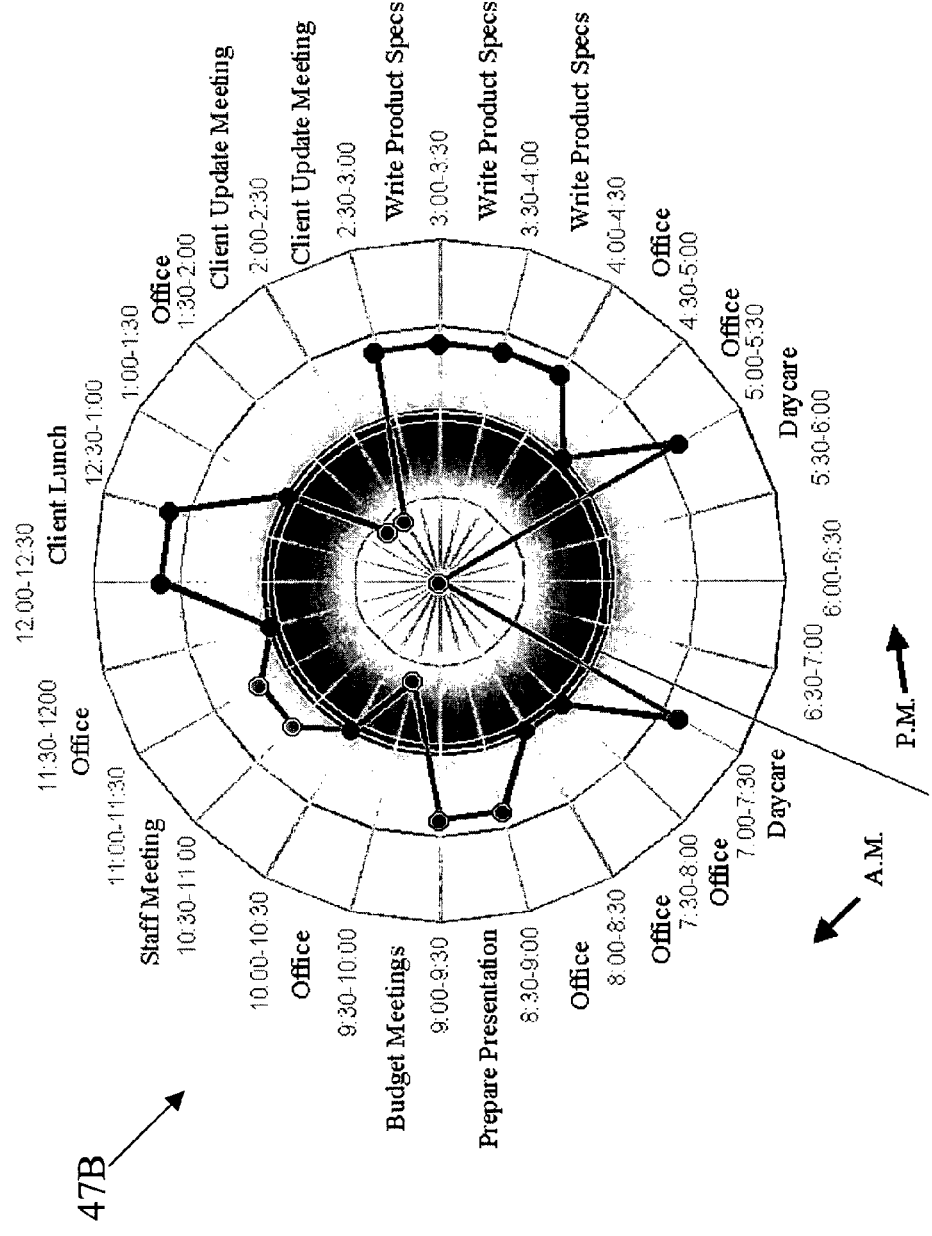

The Schedule SMT takes a totally different approach to one's schedule by showing an entire week's activities on one SMT chart. Further, all activities on the SMT have had their importance rated at the time the entry was made. FIG. 11A shows a weekly Schedule SMT 47A and FIG. 11B shows a daily schedule SMT 47B. Monthly and yearly schedule SMTs are also possible.

With these individual charts, a user can instantly see openings in their calendar during the week in question and can see meetings or activities that have a low priority rating and could be moved, while seeing activities that are very important and cannot be changed. Thus, the Schedule SMT could be fully integrated into PIMs or other contact management programs in one embodiment.

Using the Spheres within Spheres concept, a user can click on any day shown in the week schedule and see the details of their schedule for that day. The input of activities on the Schedule SMT 47A, 47B can be done at anytime by either clicking on the day and time a entry needs to be made or going to a traditional data entry screen and inputting the data there. At the time an entry is made its importance is rated on the 0-10 scale. Nodes rated under 5 are green (g), 5 is blue (b), 6 and above are orange (o) to red (r). Above 5 are very important and may not be changed, below 5 can easily be changed. Activities at 5 can be usually be changed.

The Weekly Schedule SMT shows in a glance how the week is shaping up:

Monday: Working in office until a 10:00 important meeting, in the afternoon is an important 1 to 2 meeting, some flexibility with a meeting at 4, no dinner meetings.

Tuesday: Start the day with kids to daycare at 7, have to pick them up at 5. Important 9:00 meeting, some flexibility at both 10 and 2 with an important meeting at 11. Important lunch meeting and important meeting at 3 to 4.

Wednesday: An 11:00 important meeting, some flexibility at lunch until a 4 meeting. An important dinner meeting at 7.

Thursday: Daycare day again, optional breakfast meeting. Important meeting at 9 and a lunch meeting.

Friday: All day seminar followed by dinner meeting.

Saturday: Soccer tournament from 10 to 1.

Details on any activity are instantly available by clicking or rolling over the node. By clicking on any node an activity can be added or deleted and time and/or details edited. The Schedule SMT is particular suited for use on a personal computer, PDA, cellphone, or viewed on the Web. In one embodiment, the user can click on any node at any time to see the details of any scheduled activity or to add/delete/modify an activity. This Schedule SMT is extremely easy to read as it is laid out to resemble a clock face. The user can instantly see the time of all activities by its location. Utilizing the sphere with in a sphere concept, the user can click on any day shown on the weekly (or monthly) SMT and they can view the details of the day's schedule.

The subject of the SMT 47B shown in FIG. 11B has a day starts and ends with day care. Time in the office between 8-8:30, preparation for important presentation between 8:30 and 9:30. A 9:30 budget meeting that can be changed if necessary. Staff meeting from 10:30 to 11:30. A very important client lunch meeting. From 1:30 to 2:30 is a client update meeting that is not critically important for this time and could be rescheduled. A significant block of time has been set aside for writing specs for a new product from 2:30 to 4:30. No evening meeting or activities are scheduled for this day.

Utilizing the plot overlay function of the Schedule SMT, when used by an entire group can address one of the most frustrating scheduling challenges, that of attempting to find a time when all parties in a group and/or department can meet.

This difficult, frustrating and time consuming activity is automated using the Schedule SMT. All parties of the group/department that are attempting to find a common schedule time for a meeting simply electronically send their month/weekly/daily calendar as appropriate. The SMTs are overlaid and automatically finds all potential meetings times where the importance rating is a 5 or less. A list of potential times is generated and when the time for the meeting is finalized it is automatically entered in everyone's calendar with a high importance rating of 10.

The NEAR SMT

The NEAR SMT is designed to show the NEAR (Needs, Expectations, Attitudes and Responsibilities) of all parties working on a shared project or common goal. The NEAR SMT is suitable for strategic planning sessions. In particular, on large projects the NEAR SMT would be the first step in the process of determining the scope of a project and moving to a go—no go status. The NEAR SMT is also applicable when assessing two or more companies considering a joint venture and/or merger as both companies NEAR can be overlaid and any potential for harmonics or discordance quickly seen.

Figure 12A:
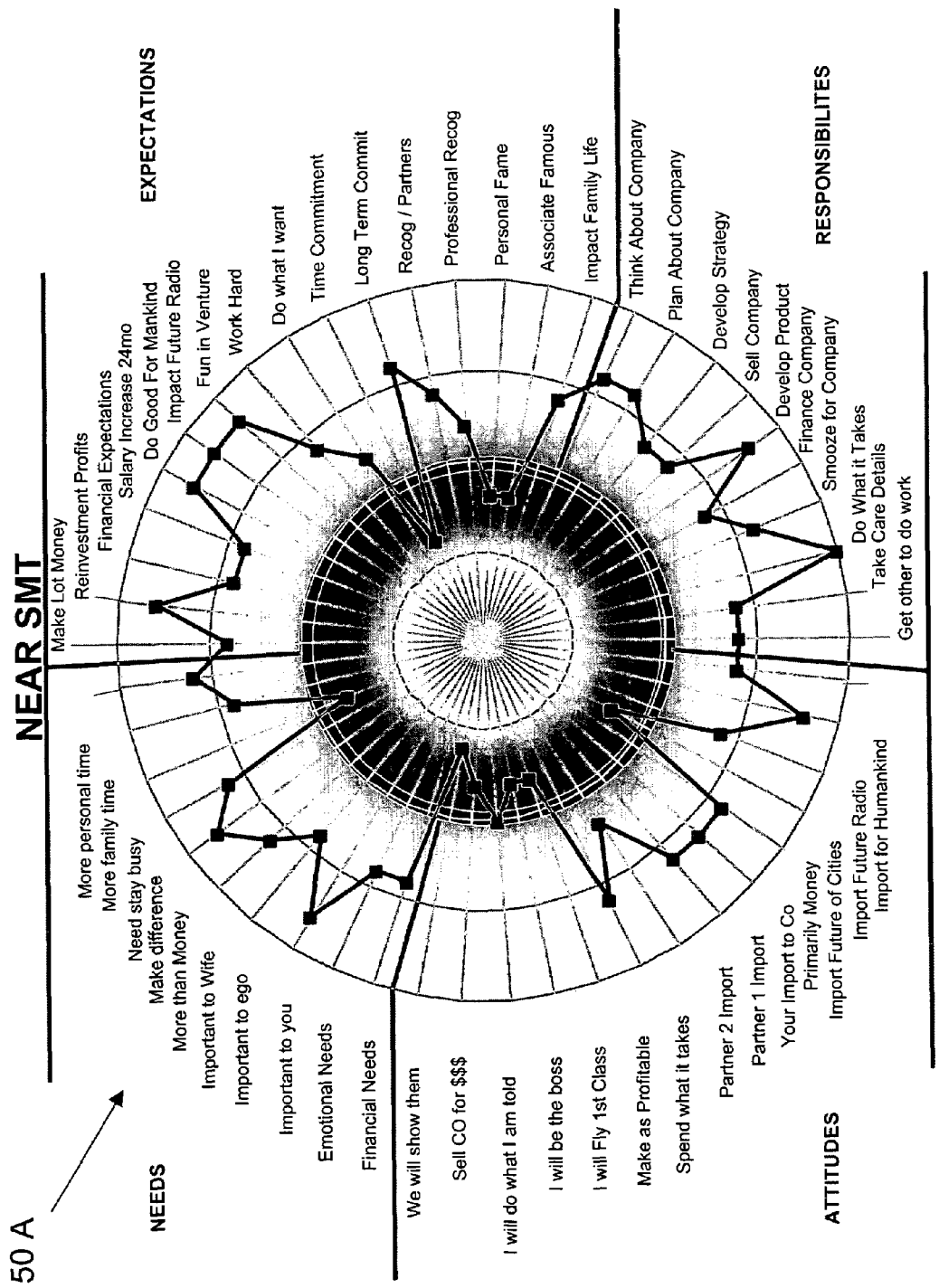
FIGS. 12A-12D are exemplary NEAR SMTs designed to assess the potential for successfully forming a new company according to the principles of the invention.
Figure 12B:
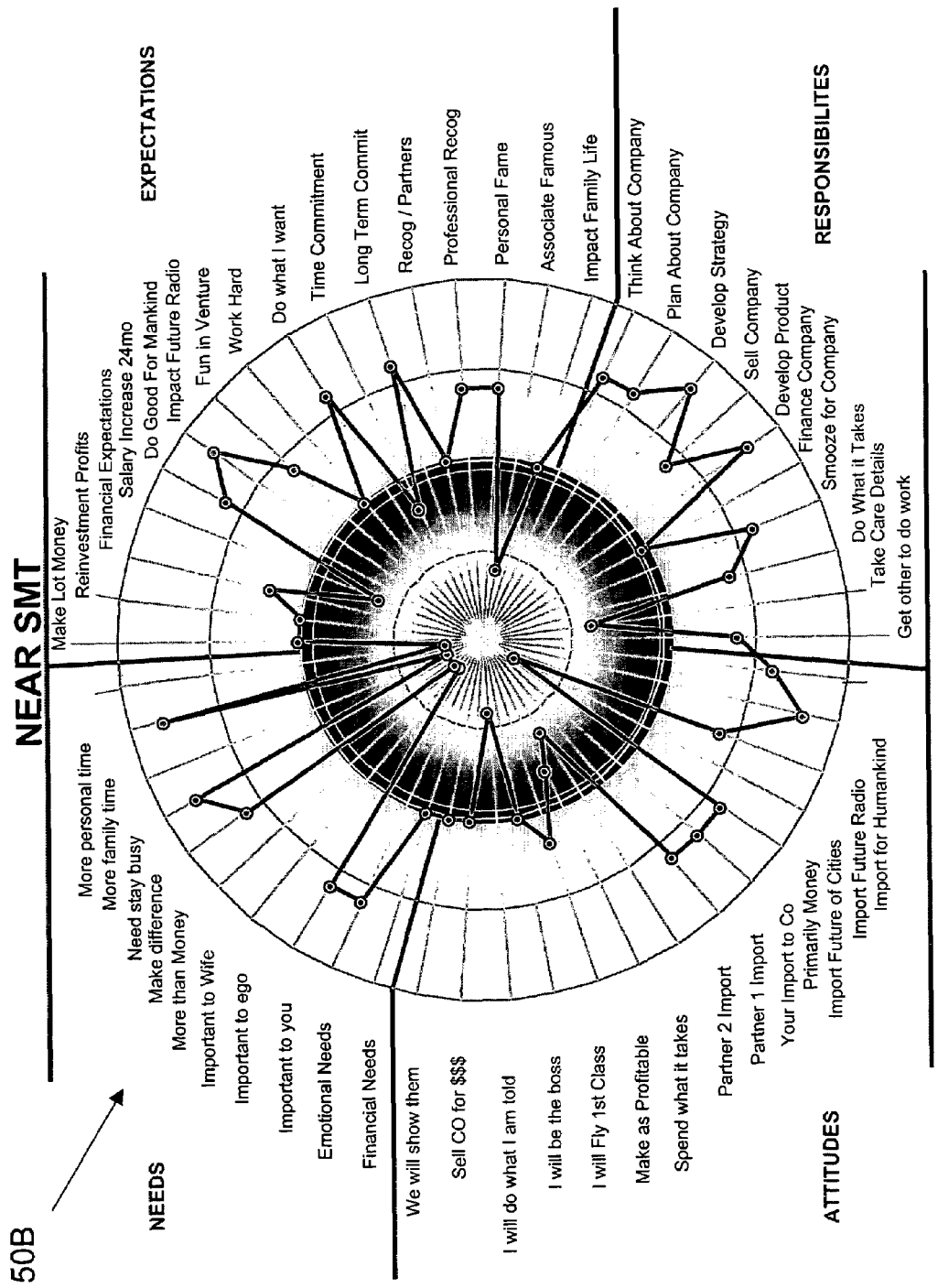
Figure 12C:
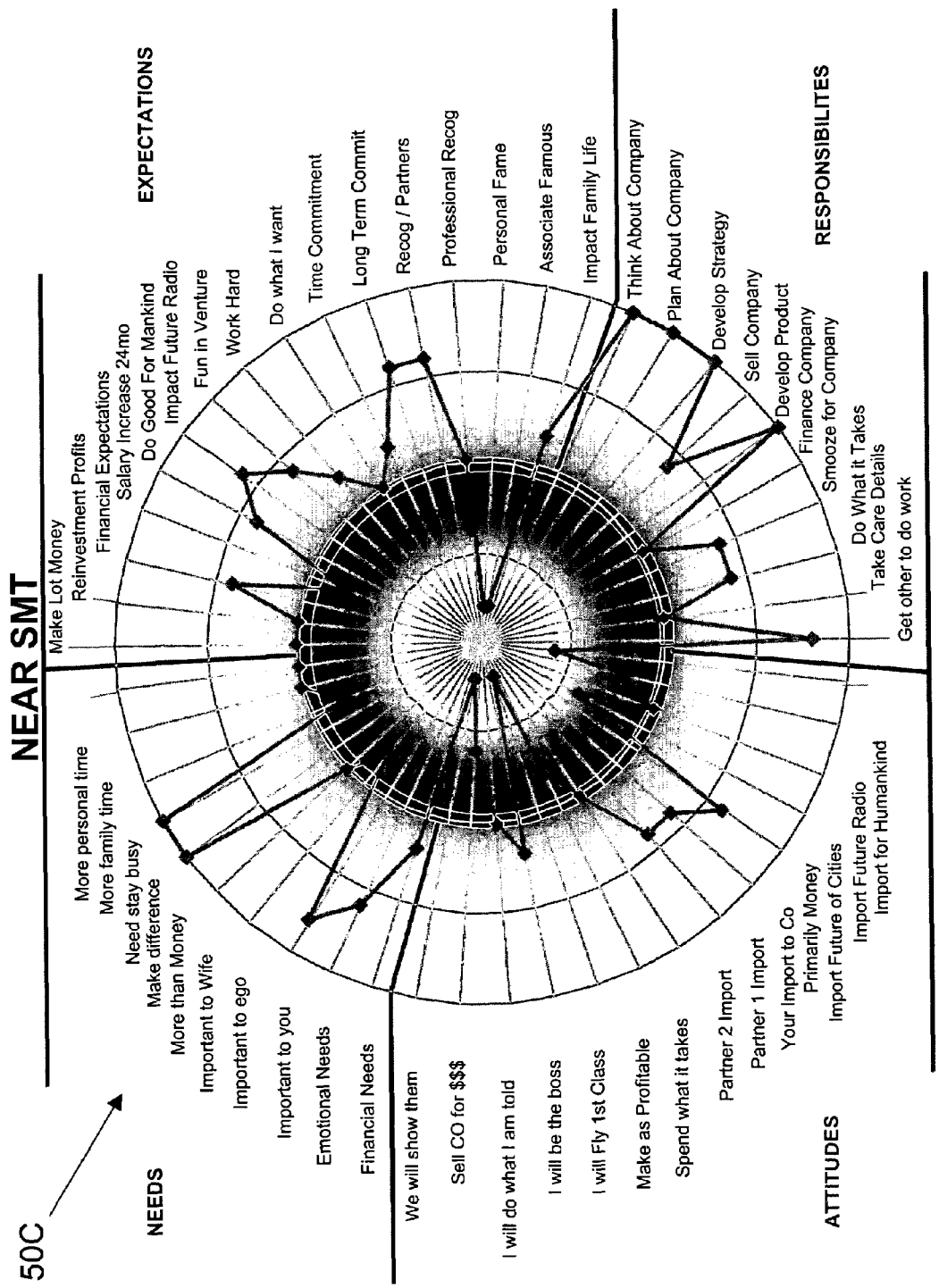
Figure 12D:
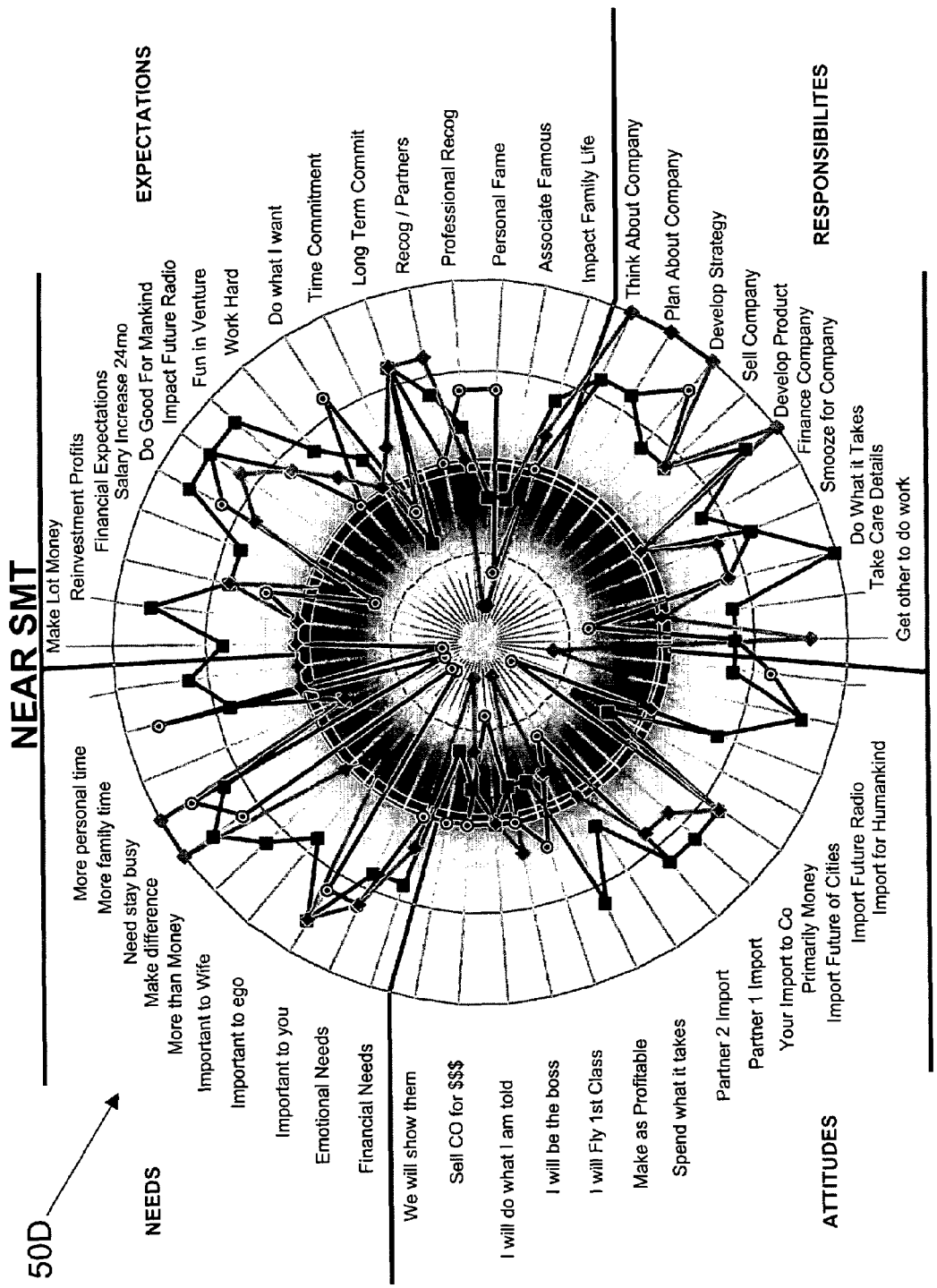

FIGS. 12A-12D illustrate examples of the NEAR SMT used to assess the potential for successfully forming a new company with three senior executives. FIG. 12D demonstrates the SMT overlap function as it includes the plots of FIGS. 12A-12C.

In the four NEAR SMTs 50A, 50B, 50C, and 50D shown, three entrepreneurs are considering launching a new company. Each party filled out a questionnaire on their NEAR for this company and how it would impact their lives, both professionally and personally. The responses of each are plotted respectively labeled, 50A, 50B, and 50C on the corresponding SMT. Each individuals plot is broken out separately for closer assessment.

In the overall NEAR SMT 50D of FIG. 12D, we find a very typical business situation. There are points of significant harmonics between the three parties on the vision and potential for the new company they are considering forming. There are areas of overlap in responsibilities that is of some concern and should be addressed before moving forward with the project. There are points of discordance to the point of almost polarization in some areas, particularly with regard to the financial structure of the organization with respect to each person's contributions. These areas have the very real potential to be fatal to the long term success of this venture.

Of the three partners for this venture, the candidate corresponding to the NEAR SMT 50A shown in FIG. 12 is the most analytical, focused on getting the job done. He has the highest personal expectations and needs of the three with regard to personal financial remuneration from this project. He also recognizes that he has significant responsibilities to the new venture.

The project is expected to have significant impact on his life and family and is seen as very important to his ego and self-worth. Of note is the fact that he is the only one of the three to specify that he feels he needs both more time with his family and more personal time. To him this is a team project, all for one-one for all, doing what it takes and splitting the rewards equally.

Turning to FIG. 12B and SMT 50B, we see another potential partner's model. This partner in the venture is already a successful businessman with another very successful company. He sees himself as the visionary for the company, though partner number 3 also sees himself in this role. This partner's personal financial expectations are not as great as partner 1 but his expectations that he would be financially compensated in direct proportion to the value he brings to the venture is fundamentally different than the financial expectations of his two potential partners. This is an issue that must be clarified in detail before moving forward.

It is worth noting that this partner's NEAR SMT pattern is the most extreme shape of the three partners. This is a very accurate reflection of this person's personality and style and should be given serious consideration by the other 2 partners.

In FIG. 12C, Partner 3 is shown as in between partners 1 and 2 in his NEAR. He is the only one of the three never to start and/or run an entrepreneurial company, his background is as a VP in international companies. He sees himself in the role of visionary which is setting up a potential conflict with partner 2. As a large corporate executive he is used to getting others to do the work and may have difficulty in getting his hands dirty in the start up phase of this company. He tends much closer to partner 1 with regard to how the financial rewards would be shared between the three.

Thus, the NEAR analysis tool and the related SMTs can be used to obtain early stage information that is invaluable to a company or organization. Resolving the conflicts between partners before a venture begins can be enormous value to the individuals and the future company.

The Financial SMT

Figure 13:
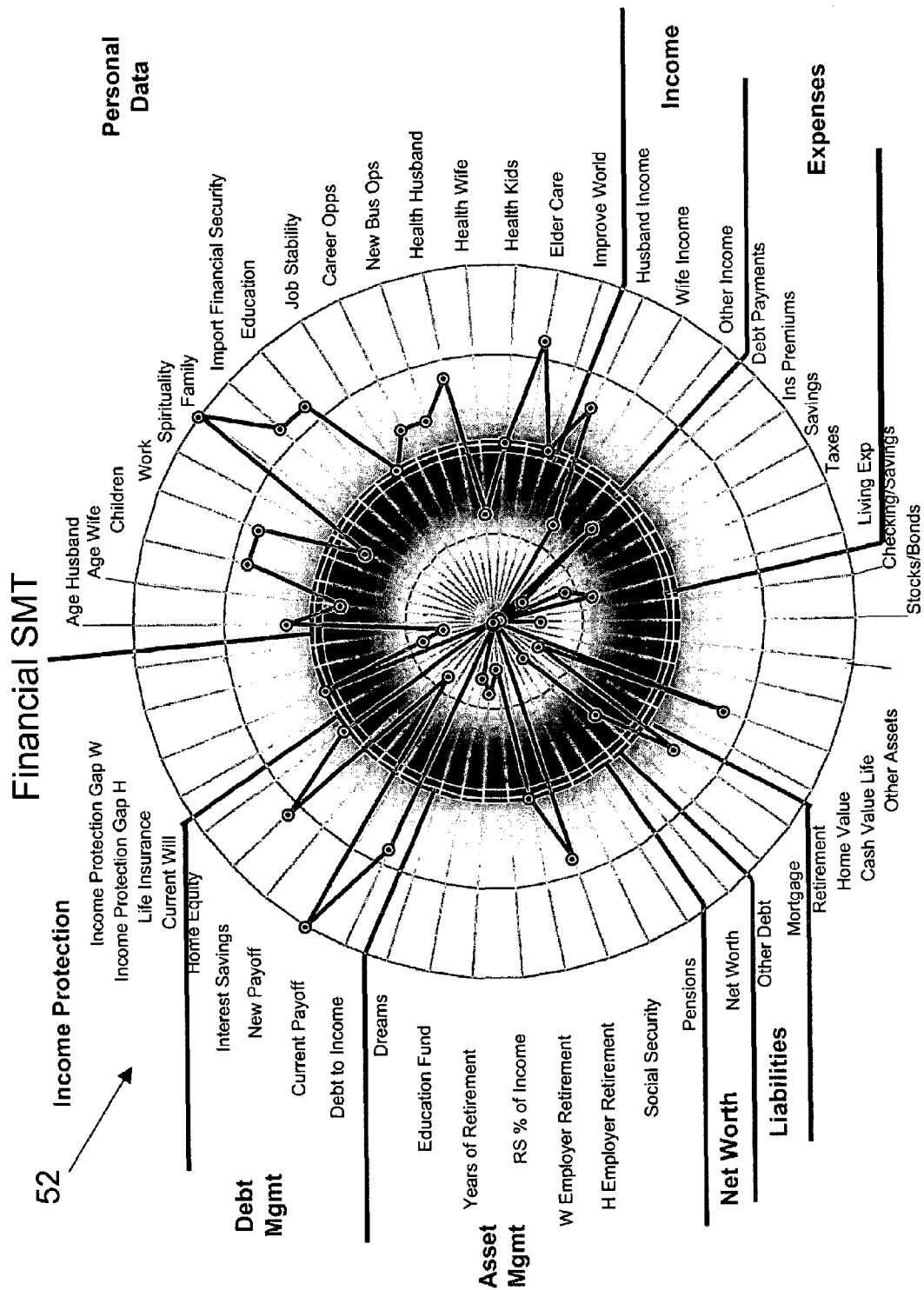
FIG. 13 is an exemplary financial SMT according to an illustrative embodiment of the invention.

The financial SMT is designed to show the entire scope of a family/individual's financial situation. The Financial SMT can be created from a detailed financial audit in one embodiment. Such an audit is performed to assess the current and projected future financial situation with regard to at least one of income, expenses, debts, assets and income protection. The audit is used as a basis for creating certain Financial SMTs. FIG. 13 shows an exemplary financial SMT 52.

The SMT 52 shown in FIG. 13 describes the financial status of a married couple. As shown, the husband is just over the halfway point in his projected life span, the wife is just under. They have over the average number of children (3). Also, they rate their family as the most important aspect of their life at a 10. Accordingly, financial security for the family is very important.

The couple has an above average education with the husband having a masters degree. The SMT 52 shows job stability as average, career opportunities are a little above average. The husband and the children are in good health. Although the wife has some health problems. The couple anticipates having to take care of their elderly parents.

The husband makes more than 60% of the total family household income (yet is severely underinsured as shown in Income Protection gap). Debts payments are high in relation to income, their only real asset is their home. However, as can be seen in the liabilities section, they owe almost the entire value of the home. This financial reality is also represented in the Debt Mgmt sector which shows home equity to be barely above the payoff.

The Asset Mgmt sector of the SMT 52 shows that they have virtually no preparation for future income needs for education and retirement. Current assets would give them less than 4 years of retirement if assets were liquidated.

In the Income Protection sector, the SMT 52 reveals that they have some minimum life insurance. Unfortunately, as is graphically shown in the two income protection nodes (H-Husband, W-wife), they have a very severe income protection gap. This gap needs to be covered to provide financial security for the family. This need is readily apparent given the couples ranking of this category in the Personal Data sector.

The Briefing Program SMT

The Briefing Program SMT assists in the process of developing, strategizing and operating in-house sales and marketing facilities commonly called executive briefing centers, or EBCs. The Briefing Program SMT guides executives, managers and staff toward a better understanding and awareness of the dynamic interconnections within a briefing program. It also helps stakeholders in the EBC see and evaluate the program in relation to the sphere of the larger organization and competing organizations.

The Briefing Program SMT enhances the EBC decision-making process and provides an ongoing assessment of the EBCs condition and effectiveness. It provides the unique ability to communicate the well-being of the program to individuals inside and outside the company who might otherwise be unfamiliar with the operations of the EBC.

Figure 14:
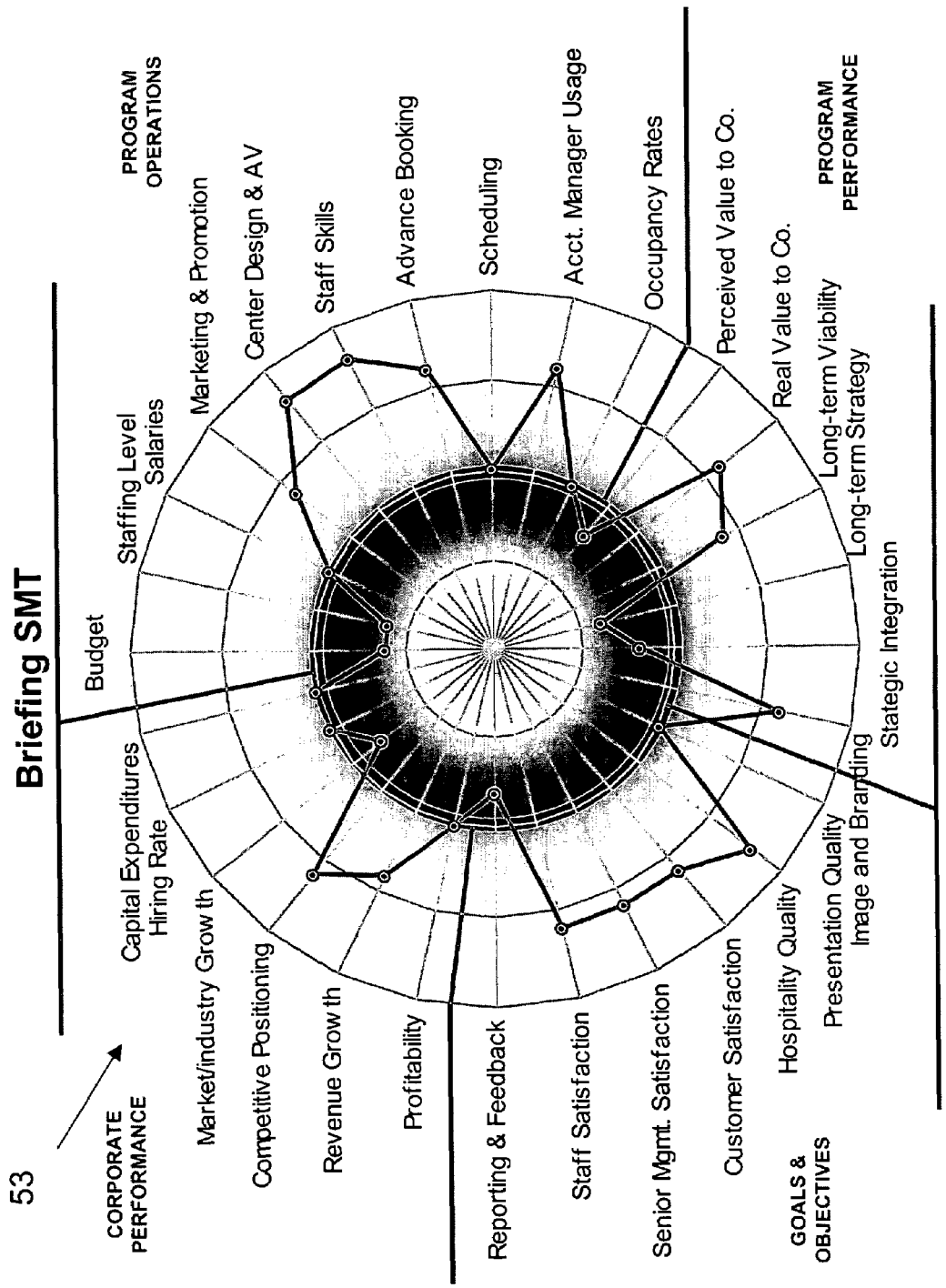
FIG. 14 is an exemplary briefing SMT according to an illustrative embodiment of the invention.

The Briefing Program SMT 53 in FIG. 14 depicts four primary sectors of nodes in which related aspects of the programs are clustered according to their relationships. In this example, the company, which operates the EBC, is increasing revenues and holding profitability at a reasonable level even though the market is shrinking or consolidating to some degree. The company is doing that on the strength of its market positioning. The industry customer base is declining, but customers view the company as a top choice. The SMT 53 visually depicts the fact that the company is growing revenues and achieving a highly competitive position without increasing hiring or capital investment beyond basic levels.

A good facility, exceptional staff, high quality hospitality and generally very high satisfaction and utilization levels suggest this center is excelling in its objectives and operations. The EBC manager is highly confident in the value the program is contributing and sees good long-term prospects.

Paradoxically, the program seems to be under-recognized by senior management for its value contributions. This would seem to be born out by the lower-than-expected or lower-than-needed budget and staffing levels.

The internal marketing and promotion seems to be working well to draw usage, but it does not seem to be affecting the perception of value by senior management. Clearly, there is a discrepancy between management satisfaction with the way the program operates and the value it contributes. The program appears to be poorly integrated into the strategic plan of the company. It does not have a long-term strategy in place. There exists a contradiction between this and the optimistic assessment of long-term viability.

If revenues are increasing, why is there not also an expansion of personnel and facilities? What does that suggest about the briefing program's position? Do the market conditions suggest that the company will need to cut costs to maintain or increase profitability? Right now, profits seem to be at a desirable level, but what if they were to fall even slightly? What would that mean to the long-term viability of the costly EBC program? What if the program were to raise its perceived value? What if the program were to become more strategically integrated?

All of these business specific questions arise from a quick visual scan of the SMT 53. As an awareness and discussion tool the briefing SMT 53 provides a convenient approach for businesses entities and management. Moreover, using this SMT 53 with other business relevant SMTs both the questions and the answers that companies require can be determined in a fast an efficient manner.

Although only certain examples are shown, the scope of the SMT is essential infinite. It is infinite in the sense that any system, individual, or idea that can be modeled or evaluated is appropriate for use with the teachings disclosed herein.

It should be appreciated that various aspects of the claimed invention are directed to portions of the systems described, the methods and the processes of the SMT disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

The invention claimed is:

1. A method for analyzing qualitative data comprising the steps of:
   providing a plurality of evaluation categories and a respective ranking system;
   providing a closed curvilinear graph in which each unit of radius corresponds to a rank in the ranking system;
   placing each evaluation category at a location on the circumference of the closed curvilinear graph;
   providing the evaluation categories and ranking system to an entity being evaluated;
   having the entity select a rank in response in each respective category;
   plotting the ranking of each respective category as a node on the closed curvilinear graph in response to the ranking by the entity; and
   connecting the nodes to form a curvilinear line on the closed curvilinear graph.

2. The method of claim 1 wherein the closed curvilinear graph is circular.

3. The method of claim 1 wherein the closed curvilinear graph is spherical.

4. The method of claim 1 wherein the closed curvilinear graph is ellipsoidal.

5. The method of claim 1 wherein the ranking is numerical.

6. The method of claim 5 wherein an expectation value for any category is set between the highest and lowest ranking for the evaluation category.

7. The method of claim 1 wherein each node is in itself a closed curvilinear graph.

8. The method of claim 1 wherein the curvilinear line links each node and each link between nodes is a directed link.

9. The method of claim 8 wherein each directed link is associated with a respective value.

10. The method of claim 9 wherein the respective value is a tensegrity factor.

11. The method of claim 1 wherein the qualitative data is data about an entity.

12. The method of claim 1 wherein the qualitative data is data about an organization.

13. The method of claim 1 wherein the qualitative data is ensemble data derived from a plurality of sources.

14. A method of qualitatively comparing the compatibility of two entities comprising the steps of:
providing a plurality of evaluation categories and a respective ranking system;
providing a closed curvilinear graph in which each unit of radius corresponds to a rank in the ranking system;
placing each evaluation category at a location on the circumference of the closed curvilinear graph;
providing the evaluation categories and ranking system to each the entity; selecting a rank in response to each respective category;
plotting, for each respective entity, the ranking of each respective category as a node on the closed curvilinear graph in response to the ranking by the entity; and
connecting the nodes to form a respective curvilinear line on the closed curvilinear graph for each entity.

15. The method of claim 14 further comprising the step of determining the similarity between the plotted nodes.

16. The method of claim 14 wherein the entities are companies contemplating merger.

17. The method of claim 14 wherein the entities are individuals in an organization.

18. The method of claim 14 wherein the entities are individuals contemplating starting a company.

19. The method of claim 14 wherein the entities are a company and its proposed investors.

20. The method of claim 14 wherein the result of the plotting is a Spherical Modeling Tool (SMT).

21. The method of claim 14 wherein at least one node corresponds to an SMT.

22. An apparatus for analyzing qualitative data comprising:
a plurality of evaluation categories and a respective ranking system;
a closed curvilinear graph in which each unit of radius corresponds to a rank in the ranking system with each of the plurality of evaluation categories being placed at a location on the circumference of the closed curvilinear graph;
an output device for providing the evaluation categories and ranking system to an entity being evaluated;
an input device for having the entity select a rank in response in each respective category; and
a display plotting the ranking of each respective category as a node on the closed curvilinear graph in response to the ranking by the entity and a curvilinear line connecting the nodes on the closed curvilinear graph.

23. An apparatus for analyzing qualitative data comprising:
means for providing a plurality of evaluation categories and a respective ranking system;
means for providing a closed curvilinear graph in which each unit of radius corresponds to a rank in the ranking system;
means for placing each evaluation category at a location on the circumference of the closed curvilinear graph;
means for providing the evaluation categories and ranking system to an entity being evaluated;
means for having the entity select a rank in response in each respective category;
means for plotting the ranking of each respective category as a node in the closed curvilinear graph in response to the ranking by the entity; and
means for connecting the nodes to form a curvilinear line on the closed curvilinear graph.

24. The apparatus of claim 23 wherein the closed curvilinear graph is circular.

25. The apparatus of claim 23 wherein the ranking is numerical.

26. The apparatus of claim 23 wherein an expectation value for any category is set between the highest and lowest ranking for the evaluation category.

27. The apparatus of claim 23 wherein the qualitative data is data about an entity.

28. The apparatus of claim 23 wherein the qualitative data is data about an organization.

29. The apparatus of claim 23 wherein the qualitative data is ensemble data derived from a plurality of sources.

* * * * *